Figure 1:
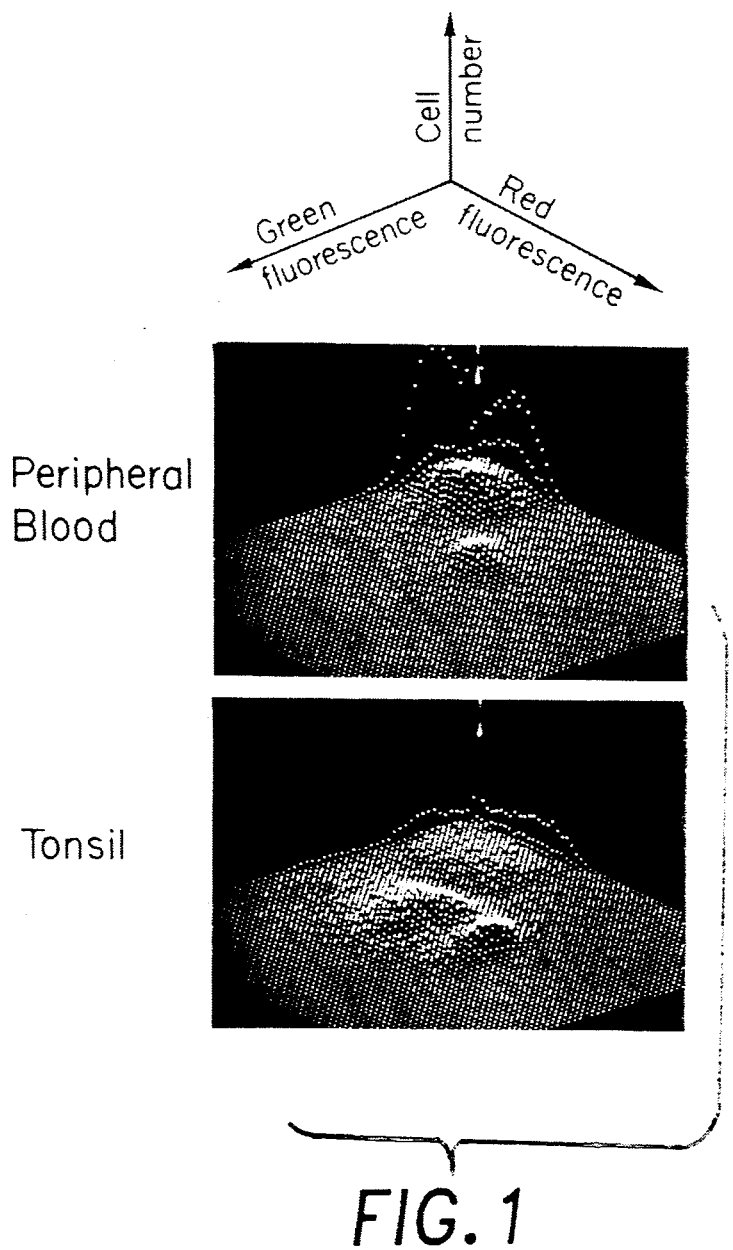

United States Patent [19]

Ledbetter et al.

[11] Patent Number: 5,247,069
[45] Date of Patent: Sep. 21, 1993

[54] LIGANDS AND METHODS FOR AUGMENTING B-CELL PROLIFERATION

[75] Inventors: Jeffrey A. Ledbetter; Edward A. Clark, both of Seattle, Wash.

[73] Assignee: Oncogen, Seattle, Wash.

[21] Appl. No.: 896,076

[22] Filed: Jun. 2, 1992

Related U.S. Application Data

[60] Division of Ser. No. 708,075, May 24, 1991, Pat. No. 5,182,368, which is a continuation of Ser. No. 873,884, Jun. 13, 1986, abandoned.

[51] Int. Cl.$^5$ .................. C07K 15/06; C07K 15/14
[52] U.S. Cl. .................... 530/350; 530/380; 530/395; 530/829
[58] Field of Search ............... 530/350, 380, 395, 829

[56] References Cited

U.S. PATENT DOCUMENTS 4,671,958  6/1987  Rodwell et al. ................. 424/85

OTHER PUBLICATIONS

Paulie, S. et al., J. Immunol., 142: 590–595, 1989.
Wang, C. Y. et al., J. Exp. Med. 149: 1424–1437, 1979.
Ambrus, J. L. Jr. et al., J. Clin. Invest. 75: 732–739, 1985.
Stamenkovie, I. et al., EMBO Journal 8(5): 1403–1410, 1989.
Ledbetter et al., 1987, J. Immunol. 138: 788–794.
Clark and Ledbetter, 1986, Proc. Natl. Acad. Sci. U.S.A. 83: 4494–4498.
Clark et al., 1985, Proc. Natl. Acad. Sci. U.S.A. 82: 1766–1770.
Golay et al., 1985, J. Immunol. 135: 3795–3801.
Peters et al., 1988, J. Exp. Med. 168: 1225–1235.
De Franco et al., 1985, J. Immunol. 135: 87–94.
Jung and Fu, 1984, J. Exp. Med. 160: 1919–1924.
Swain et al., 1983, J. Exp. Med. 158: 822–835.
Maizel et al., 1982, Proc. Natl. Acad. Sci. U.S.A. 79: 5998–6002.
Muraguchi et al., 1985, J. Exp. Med. 161: 181–197.
Zubler et al., 1984, J. Exp. Med. 160: 1170–1183.
Chan et al., 1985, Int. J. Cancer 36: 329–336.
Dower et al., 1985, J. Exp. Med. 162: 501–515.
Paulie et al., 1985, Cancer Immunol. Immunother, 20: 23–28.
Koho et al., 1984, Cancer Immunol. Immunother 17: 165–173.
Wang et al., 1984, J. Immunol. 133: 684–691.
Zipf et al., 1983, J. Immunol. 131: 3064–3072.
Slovin et al., 1982, Proc. Natl. Acad. Sci. U.S.A. 79: 2649–2653.
Ledbetter and Herzenberg, 1979, Immunol. Rev. 47: 63–90.

*Primary Examiner*—Kay K. Kim
*Assistant Examiner*—Julie Krsek-Staples
*Attorney, Agent, or Firm*—Pennie & Edmonds

[57] ABSTRACT

A new B-cell receptor, Bp50, a 50 kilodalton polypeptide, that functions in B-cell proliferation is described. Ligands such as lymphokines, antibody molecules or the Fv fragments of antibody molecules that bind to Bp50 and augment the proliferation of activated B-cells can be used to regulate B-cell proliferation or differentiation.

1 Claim, 9 Drawing Sheets

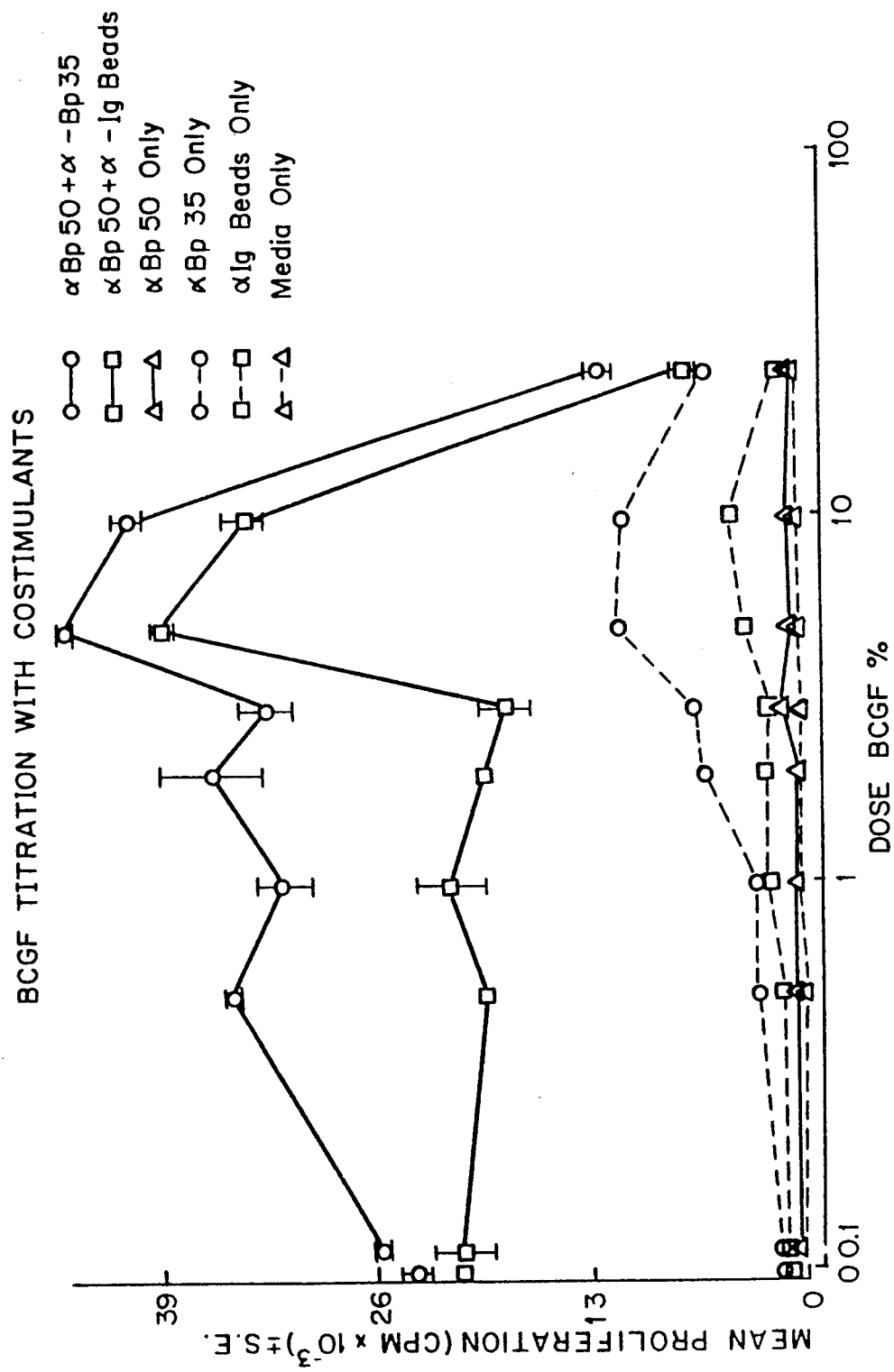

LIGANDS AND METHODS FOR AUGMENTING B-CELL PROLIFERATION

This is a divisional application under 37 C.F.R. §1.60 of U.S. Ser. No. 07/708,075, filed May 24, 1991, now U.S. Pat. No. 5,182,368 which is a continuation of U.S. Ser. No. 06/873,884, filed Jun. 13, 1986 now abandoned.

TABLE OF CONTENTS

1. Introduction
2. Background of the Invention
3. Summary of the Invention
3.1. Definitions
4. Description of the Figures
5. Detailed Description of the Invention
5.1. Methods Used to Characterize the Bp50 Receptor
5.2. Characterization of the Bp50 Receptor
    5.2.1. Identification of a B-Cell Specific 50 kDa Cell Surface Marker, Bp50
    5.2.2. Expression of Bp50 is Restricted to B-Cells
5.3. Augmentation of B-Cell Proliferation with Anti-Bp50 Antibody
    5.3.1. Anti-Bp50 mAb Augments Proliferation Only after B-Cells are Activated by Anti-Bp35 or Anti-u Antibodies
    5.3.2. Anti-Bp50 mAb do not Activate B-Cells out of $G_0$ but do Induce Activated B-Cells to Progress Through the Cell Cycle
    5.3.3. Optimal Conditions for Augmenting B-Cell Proliferation with Anti-Bp50 Antibodies
    5.3.4. Differences Between Anti-Bp50 and BCGF (Low) Activity
5.4. Uses of Anti-Bp50 Ligands and Bp50
    5.4.1. Bp50 Receptor and Uses of Ligands Such as Anti-Bp50 to Augment B-Cell Proliferation
    5.4.2. Modified Ligands Used for Iummunosuppression or Treatment of Malignancies
    5.4.3. Other Uses of Ligands and Bp50
6. Deposit of Cell Lines

1. INTRODUCTION

The present invention is directed to ligands, such as antibody molecules or fragments of antibody molecules or other ligands such as lymphokines which bind to a 50kDa B-cell surface marker, herein referred to as Bp50, that functions in B-cell proliferation but not in early B-cell activation. The present invention is also directed to the Bp50 B-cell antigen itself. In a particular embodiment of the present invention, a monoclonal antibody, G28-5, is described that defines Bp50 and appears to play a role in the proliferation of activated B-cells but has no detectable effect on the proliferation of resting B-cells.

The ligands, such as antibodies, lymphokines and fragments thereof of the present invention can be used to direct and regulate human B-cell proliferation and/or differentiation. In addition, the ligands of the present invention may be modified by the attachment of other compounds which can be used in the treatment and/or detection of malignant cells that express the Bp50 antigen.

2. BACKGROUND OF THE INVENTION

The activation of resting B-cells from $G_0$ to $G_1$ phase of the cell cycle and the subsequent induction of activated B-cells to proliferate are distinct steps requiring distinct regulatory mechanisms. Some agents, including murine B-cell stimulating factor-pl (BSF-pl) (Rabin, et al., 1985, Proc. Nat. Acad. Sci. USA 82, 2935-2939) or low doses of anti-immunoglobulin (anti-Ig) (DeFranco, et al., 1985, J. Immunol. 135:87-94; Wetzel, et al., 1984, J. Immunol. 133:2327-2332; DeFranco, et al., 1982, J. Exp. Med. 155:1523-1536; Muraguchi, et al., 1984, J. Immunol. 132:176-180), are "activation" or "competence" factors. That is, they induce B-cells to enlarge, synthesize more RNA, and enter $G_1$, but alone they do not induce DNA synthesis in B-cells. Other "growth" factors, such as human B-cell growth factor (BCGF) and interleukin-2 (IL-2) cause activated B-cells to traverse the cell cycle and enter S phase but do not trigger resting B-cells (Kehrl, et al., 1984, Immunol. Rev. 18:75-96; Muraguchi, et al., 1984, J. Immunol. 132:176-180; Zubler, et al. 1984, J. Exp. Med. 160:1170-1183; Jung, et al., 1984, J. Exp. Med. 160:1597-1604).

A number of factors that promote the growth of B-cells have now been described by investigators of both murine and human systems. These include B-cell growth factors (BCGF) derived from several different sources including T-cell lines or hybridomas, B-cell lines, or dendritic cells. Although both interleukin-1 (IL-1) and interleukin-2 (IL-2) have been shown to augment B-cell growth, they apparently are distinct from certain BCGFs. For instance, monoclonal antibodies (mAb) to a murine BCGF (O'Hara, et al., 1985, Nature (Lond.) 315:333) or human BCGF (Ambrus, et al., 1985, J. Exp. Med. 162:1319) block BCGF activity but not IL-1 or IL-2 activity. Although distinct from IL-1 or IL-2, the BCGFs themselves appear to be heterogeneous based on biochemical data and differential activity on different B-cell subsets or costimulation assays. For instance, 60-kilodalton (kDa) high-molecular-weight human BCGF, BCGF (high), has been identified that is distinct from a 12-kDa low-molecular-weight form, BCGF (low) (Ambrus, et al., 1985, J. Clin. Invest. 75:732). The cDNA encoding a 20-kDa murine BCGF, tentatively designated B-cell stimulating factor pl (BSF-pl), has recently been cloned and sequenced (Noma et al., 1986, Nature 319:640). The recombinant lymphokine not only has BCGF activity but can also activate resting B-cells and induce the differentiation of $IgG_1$ producing cells; thus it differs from human BCGF (high) and BCGF (low) both in its molecular weight and in its range of activity.

These activation and growth signals presumably regulate cells by interacting with specific B-cell surface structures. In addition to the antigen-specific signal through surface Ig, several other candidate B-cell surface polypeptides have been identified that may in some way function in the activation or growth of B-cells. For instance, the cell surface receptors for IL-1 (Dower, et al., 1985, J. Exp. Med. 160:501) and IL-2 (Robb et al., 1984, J. Exp. Med. 160:1126) have been characterized, and recently functional IL-2 receptors have been identified on B-cells (Zubler, et al., 1984, J. Exp. Med. 160:1170; Jung, et al., 1984, J. Exp. Med. 160:1597; Muraguchi, et al., 1985, J. Exp. Med. 161:181). However, receptors for B-cell growth and activation factors have yet to be fully characterized. Several candidate B-cell surface polypeptides have been identified that may in some way function in the activation or growth of B-cells. For example, Subbarao and Mosier (Subbarao, et al., 1983, Immunol. Rev. 69:81-97) found that monoclonal antibodies (mAb) to the murine B-cell antigen Lyb2 activate B-cells, and recently evidence has been presented suggesting Lyb2 may be the receptor for BSF-pl (Yakura, 1985, Fed. Proc. 44:1532). Similarly, we have found that appropriate mAb (1F5) to a 35 kDa polypeptide, Bp35, activates human B-cells from $G_0$ into $G_1$ (Clark, et al., 1985, Proc. Nat. Acad. Sci. USA 82:1766-1770; Gollay, et al., 1985, J. Immunol. 135:3795-3801). Aggregated C3d or antibodies to the 140 kDa C3d receptor, Bp140, cause proliferation of B-cells that are T-cell dependent (Melchers, et al., 1985, Nature 317:264-267; Nemerow, et al., 1985, J. Immunol. 135:3068-3073; Frade et al., 1985, Eur. J. Immunol. 15:73-76). Although BCGFs have been identified in both mouse and man, the receptors for these factors have not yet been isolated. Wang and coworkers (Wang, et al., 1979, J. Exp. Med. 149:1424-1433) made a polyclonal antisera that identified a 54-kDa polypeptide (gp54) on human B-cells and showed that the rabbit antisera to gp54 induced tonsillar B-cells to divide. Recently, Jung and Fu (Jung, et al., 1984, J. Exp. Med. 160:1919-1924) isolated a mAb (AB-1) to a 55-kDa antigen restricted to activated B-cells that blocks BCGF-dependent proliferation. However, whether or not either anti-gp54 or AB-1 recognize a BCGF receptor is not yet known.

3. SUMMARY OF THE INVENTION

The present invention is directed to ligands which (a) bind to Bp50, a 50kDa B-cell specific surface polypeptide described herein, and (b) augment the proliferation of activated B-cells. The invention is also directed to the Bp50 antigen itself, which is defined by monoclonal antibody G28-5 and functions in proliferation of activated B-cells. In addition the invention is directed to ligands which bind to Bp50, but do not demonstrate a biological effect or function such as augmentation of the proliferation of activated B-cells.

The ligands of the present invention include antibody molecules, monoclonal antibody molecules and fragments of these antibody molecules which contain the antigen combining site or chemically modified antibodies and fragments; such fragments include but are not limited to the Fv, Fab, F(ab')$_2$, Fab' and the like. In addition, the ligands of the present invention comprise lymphokines, which can include but are not limited to human B-cell growth factors as well as chemically modified lymphokines. The ligands of the present invention can be chemically modified, for example by linking or coupling a compound to the ligand. Such compounds include but are not limited to cytotoxic agents, therapeutic agents, chemotherapeutic agents, labels such as radiolabels, dyes, enzymes, radioopaque compounds, and the like. The ligands of the present invention can in their modified or unmodified form, be used to direct, regulate and modify human B-cell proliferation and/or differentiation.

The present invention is based upon the discovery that two human B-cell differentiation antigens, Bp35 and the B-cell antigen described herein, Bp50, apparently play distinctive roles as signal receptors in B-cell activation. Monoclonal antibodies (mAb) to Bp35 and Bp50 both deliver positive signals to B-cells that stimulate their transition through the cell cycle. MAb to Bp35, like anti-Ig antibodies, functions principally to activate resting B-cells to become competent to enter the $G_1$ phase of the cell cycle. In contrast, a monoclonal antibody described herein or its F(ab')$_2$ fragment to Bp50, a 50-kDa polypeptide expressed on all B-cells, functions to stimulate activated B-cells to traverse the cell cycle and augments the proliferation of activated B-cells. Monoclonal antibodies to Bp35, like anti-Ig antibodies, activate tonsillar B-cells and induce low levels of B-cell proliferation. In contrast, anti-Bp50 monoclonal antibody alone neither activates B-cells nor induces B-cells to proliferate, but together with anti-Bp35 or anti-Ig antibodies, augments B-cell proliferation. In this respect the action of anti-Bp50 antibody resembles the activity of B-cell growth factors (BCGF). As little as 0.05 ug/ml of anti-Bp50 is needed to augment proliferation and, like BCGF, anti-Bp50 is effective even when added 12 to 24 hours after B-cells are activated with anti-Ig or anti-Bp35. Without additional exogenous signals, anti-Bp35 and anti-Bp50 antibodies together induce strong proliferation of purified resting B-cells. These results suggest that the Bp35 and Bp50 surface molecules function in the regulatory control of B-cell activation and progression through the cell cycle. Because of the significance anti-Bp35 and like molecules have on the effect and action of the ligands of the present invention, Clark et al., 1985, Proc. Natl. Acad. Sci. (USA) 82:1766-1770 is incorporated by reference herein.

Although the activity of anti-Bp50 resembles that of BCGF (low) since both anti-Bp50 and BCGF (low) are costimulatory with the same agents but not with each other and both anti-Bp50 and BCGF (low) affect only activated B-cells and work in a soluble form, the activity of anti-Bp50 can be distinguished from the activity of BCGF (low), since the proliferation of B-cells stimulated with optimal amounts of anti-Bp50 and anti-Bp35 (or anti-Ig) can be augmented further with BCGF (low) and both blood B-cells and certain B-cell lymphomas respond differently to anti-Bp50 versus BCGF. For optimal activity, anti-Bp50 should be added within 12 hours of B-cell activation, whereas BCGF (low) retains optimal activity even when added 24 hours after activation. In addition, Bp50 is expressed on all B-cells while receptors or BCGF (low) are restricted to activated B-cells. Thus anti-Bp50 and BCGF (low) may coordinately regulate B-cell growth, but apparently do so through distinct signals.

In one embodiment of the present invention, the ligands which bind to Bp50 and augment the proflliferation of activated B-cells can be used to increase an immune response. For example, these ligands which bind Bp50 can be used as an "adjuvant" to increase an immune response to a vaccine. Alternatively, these ligands can be used to increase the immune response of an immunosuppressed individual.

In another embodiment, the ligands of the invention can be chemically modified so that the cells to which the ligands bind are killed. Since all B-cells express the Bp50 antigen, this approach would result in suppression of the immune response. For example, a cytotoxic drug linked to a ligand of the present invention can be used in vivo to cause immunosuppresion in order to cross histocompatibility barriers in transplant patients; alternatively, these modified ligands may be used to control autoimmune diseases.

In another embodiment of the present invention, malignancies such as tumor cells that express Bp50 can be treated using a ligand of the invention linked to a chemotherapeutic agent useful in treating such neoplastic disease. These modified ligands can be used in vivo to direct the chemotherapeutic agent to any type of malignant cell which expresses the Bp50 antigen including cells which are not B-cells but which do express Bp50. When using the ligands of the invention which augment B-cell proliferation, a particular advantage should be realized when treating B-cell malignancies where the chemotherapeutic agent linked to the ligand comprises one that is more effective in killing proliferating cells; in this instance a potentiation of the drug action should be obtained.

Alternatively, the ligands of the invention can be used in vitro to identify or separate cells which express the Bp50 antigen and/or to assay body fluids for the presence of the Bp50 antigen which may or may not be shed. In addition, the ligands of the invention can be used in vivo in order to image cells or tumors which express the Bp50 antigen.

The purified Bp50 antigen of the present invention can be used to make antibodies and to make or design other ligands of the invention. In addition the Bp50 antigen could be used in assays such as diagnostic immunoassays. Moreover, Bp50 itself may be used as a mediator of cell immunity in vivo or in vitro.

3.1. DEFINITIONS

As used herein, the following abbreviations will have the meanings indicated:

AO = acridine orange
BCGF = B-cell growth factor
BCGF (high) = a 60 kDa human BCGF
BCGF (low) = a 12 kDa human BCGF
Bp35 = a 35 kDa B-cell specific surface polypeptide (CD20) defined by mAb 1F5
Bp50 = a 50 kDa B-cell specific surface polypeptide defined by mAb G28-5
Fv = the variable region or antigen-combining site of an antibody molecule. This may be any fragment which contains the idiotype of the molecule including but not limited to the Fab, F(ab')2, Fab', and the like.
IF = immunofluorescence
Ig = immunoglobulin
IL-1 = interleukin 1
IL-2 = interleukin 2
kDa = kilodalton
mAb = monoclonal antibody
SDS-PAGE = sodium dodecyl sulphate-polyacrylamide gel electrophoresis
TPA = 12-0-tetradecanoylphorbol-13 acetate

4. DESCRIPTION OF THE FIGURE

FIG. 1. Expression of Bp50 is restricted to Bp35±B-cells. Two-color flow cytometric analysis of 50,000 cells was performed as described (Clark, et al., 1985, Proc. Nat. Acad. Sci. USA 82:1766-1770). The data are plotted as cell number versus log of green fluorescence and log of red fluorescence where 4-5 dots represent approximately a doubling of fluorescence. The data are presented to show autofluorescent negative cells. PE (red) -anti-Bp35 (1F5) versus FITC (green) -anti-Bp50 (G28-5) staining shows that all Bp50+ cells are also Bp35+.

FIG. 2 (A and B). Biochemical comparison of Bp50 polypeptide with other B-cell surface antigens. Immunoprecipitation of Bp50 from surface $^{125}$I-labeled tonsillar cells was performed as described. Isolated antigens were electrophoresed on 10% SDS polyacrylamide slab gels without reduction. Gels were visualized with autoradiography and intensifying screens. Panel A: lane 1, anti-Bp50 (G28-5); lane 2, anti-Bp95 (G28-8); lane 3, sepharose-goat anti-mouse Ig only. Exposure time: 4 days. Panel B: lane 1, anti-Bp50 (G28-5); lane 2, anti-Bp45 (BLAST-2); lane 3, anti-Bp39 (G28-1); lane 4, anti-Bp39 (41-H16); lane 5, sepharose-goat anti-mouse Ig only. An exposure time of 2 days was selected so that the bands in lanes 2 to 4 were not overexposed and could be clearly distinguished relative to Bp50. One of three experiments.

Figure 3:
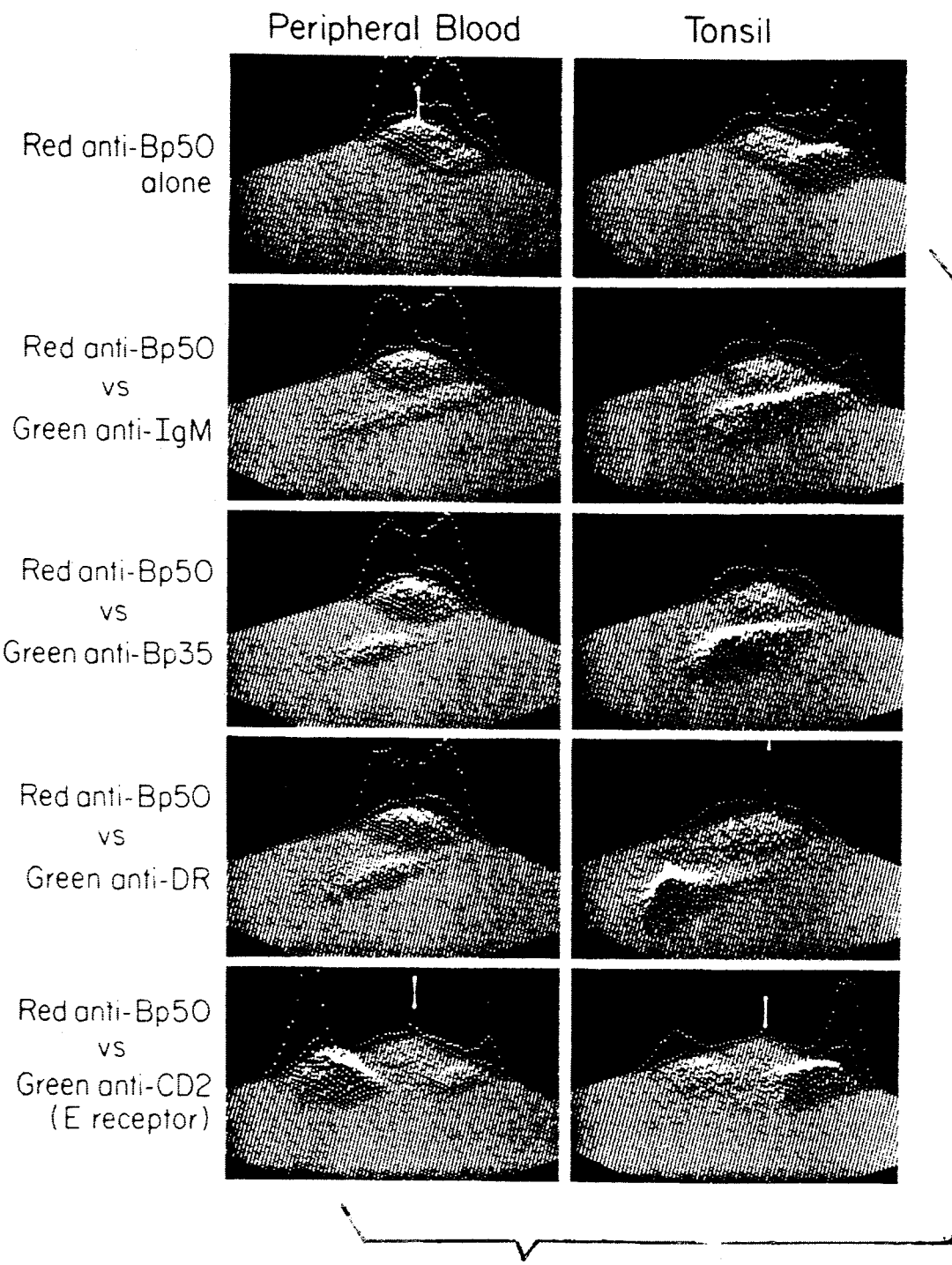

FIG. 3. Two-color immunofluorescence analysis of Bp50 expression. Peripheral blood or tonsillar mononuclear cells were isolated by centrifugation on Ficoll and stained with PE (red)-conjugated G28-5 (anti-Bp50) in combination with fluorescein (green)-conjugated reference antibodies, including 2C3 (anti-IgM); 1F5 (anti-Bp35); HB10a (anti-DR); and 9.6 (anti-CD2, E receptor). Cells were analyzed with a FACS IV fitted with four decade log amplifiers in both red and green dimensions. Forward and right angle light scatter was used to gate out monocytes. Unstained cells are positioned at the back of the grid; red fluorescence is to the right and green fluorescence is to the left.

Figure 4:
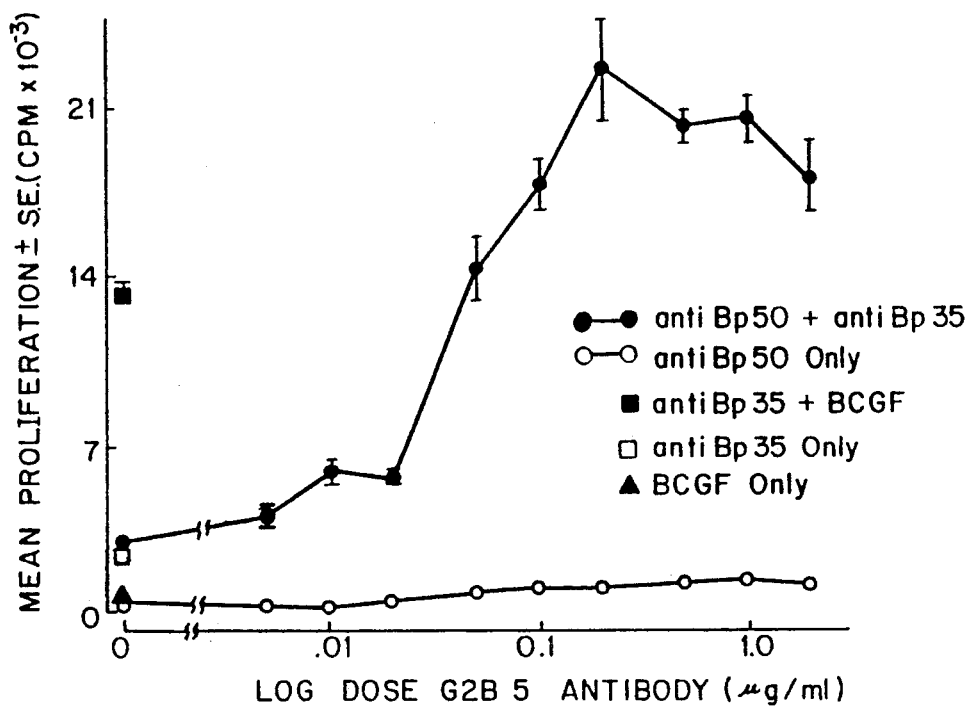

FIG. 4. Dose response curves for augmentation of proliferation of dense tonsillar Er- B-cells by anti-Bp50 antibodies as indicated: Media only; anti-Bp50 only anti-Bp35 (5 ug/ml) only; BCGF only; anti-Bp35 plus BCGF; anti-Bp35 plus graded doses of anti-Bp50. Mean proliferation±standard error of quadruplicate samples was measured on day 3.

Figure 5:
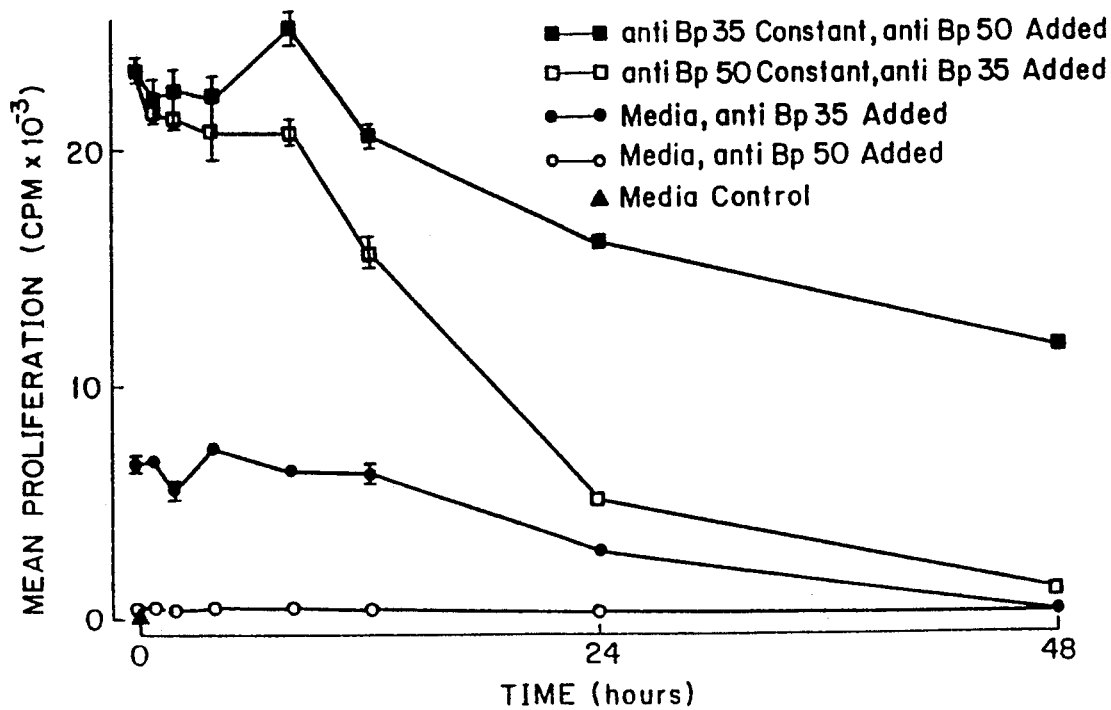

FIG. 5. Anti-Bp50 mAb are most effective at augmenting proliferation if added after a B-cell activation signal. Dense tonsillar Er- B-cells were incubated for 4 days with media only, anti-Bp50 (0.5 ug/ml) added at different times after incubation, anti-Bp35 (5 ug/ml) added at different times after incubation; anti-Bp50 kept constant to which anti-Bp35 was added later at different times; anti-Bp35 kept constant to which anti-Bp50 was added to cultures at different times. During the last 10 hr $^3$H-thymidine was added and its incorporation was measured.

FIG. 6 (A-C). Comparison of the ability of anti-Bp35 and anti-Bp50 to induce resting tonsillar B-cells to leave the G$_0$ stage of the cell cycle. Day 3 post treatment media only (_), anti-Bp35 only (-----); and Ig only (.....), A, no additional additives; B, anti-Bp50 (0.5 ug/ml) added to each group; C, 5% BCGF added to each group. Data is plotted as relative cell number versus log of AO red fluorescence (RNA).

Figure 7:
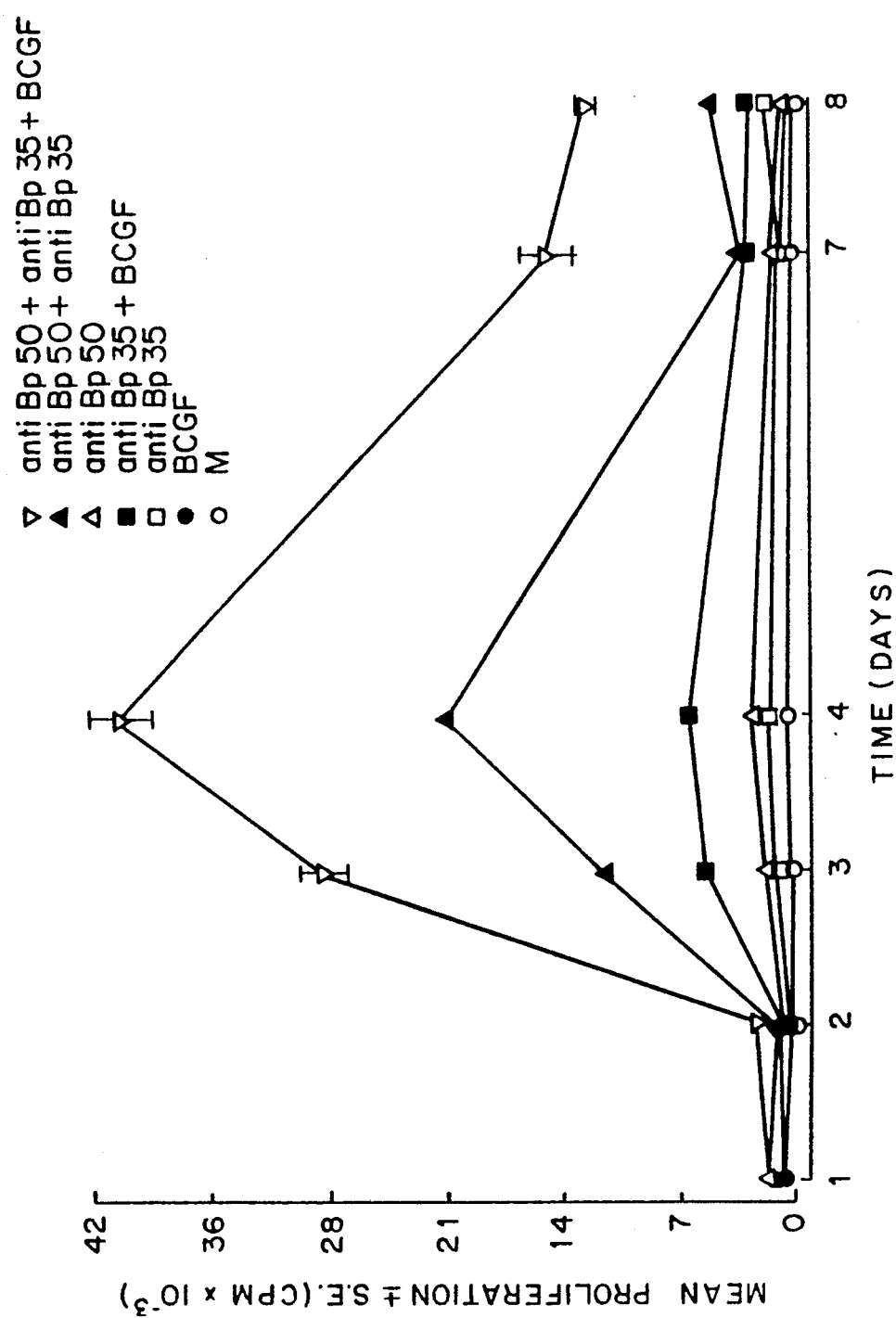

FIG. 7. Kinetics of B-cell proliferation after stimulation with anti-Bp50 versus BCGF. Dense tonsillar E-B-cells were stimulated with media alone; 10% BCGF only; anti-Bp35 only; anti-Bp50 only; anti-Bp35+10% BCGF; anti-Bp35 +anti-Bp50; and anti-Bp35+anti-Bp50+10% BCGF. Proliferation was measured on the days indicated by an 18-hour pulse of $^3$H thymidine. Proliferation was measured in quadruplicate and standard errors are shown. One of three experiments.

FIG. 8 (A and B). Times after anti-Bp35 stimulation when anti-Bp50 (A) or BCGF (B) optimally augment proliferation. Dense tonsillar E- B-cells were stimulated as shown and proliferation was measured by an 18 hour pulse of 3H thymidine on day 3. Media; anti-Bp35 only added at times indicated; anti-Bp50 or BCGF only; anti-Bp35 added at start of culture followed by addition of anti-Bp50 or BCGF at times indicated; anti-Bp50 or BCGF added at start of culture followed by anti-Bp35. One of two experiments. Proliferation was measured in quadruplicate and standard errors are shown. Doses used: anti-Bp35, 5 ug/ml; anti-Bp50, 0.2 ug/nl; BCGF (low) 5%. Concentrations used were as follows: anti-Bp35, 5 ug/ml; anti-Bp50, 0.2 ug/ml; BCGF, 5%.

FIG. 9. Anti-Bp50 and BCGF have additive effects on B-cell proliferation. Dense tonsillar E- B-cells were stimulated with graded doses of BCGF (low) together with anti-Bp50 only; anti-Bp35 only; anti-Ig-beads only ; anti-Bp35+anti-Bp50; or anti-Bp50+anti-Ig. Proliferation was measured on day 3 after stimulation with an 18-hour pulse of $^3$H thymidine. Proliferation was measured in quadruplicate and standard errors are shown. One of four experiments. Doses used $10^6$ cells anti-Bp35, 5 ug/ml; anti-Bp50, 0.2 ug/ml; anti-Ig-beads, 50 ug/ml.

FIG. 10 (A-D). Comparative effects of anti-Bp50 and BCGF on normal and malignant B-cells. Peripheral blood E- B-cells (A) or dense tonsillar E- B-cells (C) were stimulated with or without TPA (75 ng/ml) in the presence of 10% BCGF or 1 ug/ml anti-Bp50. Two separate B-cell lymphomas (panels B and D) were stimulated in the same way. Proliferation was measured on day 3 by incorporation of $^3$H thymidine during a 12-hour pulse. Proliferation was measured in quadruplicate and standard errors are shown.

5. DETAILED DESCRIPTION OF THE INVENTION

The present invention is directed to ligands which (a) bind to Bp50, a 50kDa B-cell specific surface polypeptide, and (b) augment the proliferation of activated B-cells. The invention is also directed to the Bp50 antigen itself, which is defined by mAb G28-5 and functions in B-cell proliferation. In addition, the invention is directed to ligands which bind to Bp50 but do not demonstrate a biological effect or function such as augmentation of proliferation of activated B-cells.

The ligands of the present invention include antibody molecules, monoclonal antibody molecules and fragments of these antibody molecules which contain the antigen combining site that binds to the Bp50 receptor including chemically modified antibodies and fragments; such fragments include but are not limited to the Fv, Fab, F(ab')$_2$, Fab' and the like. In addition, the ligands of the present invention comprise lymphokines, which bind to the Bp50 receptor. These may include but are not limited to BCGFs as well as chemically modified lymphokines and the like. The ligands of the invention can be used in their modified or unmodified forms to modulate and regulate immune responses and in the therapy of malignancies which express the Bp50 antigen. These uses are discussed in more detail in Section 5.4 below.

Where the ligand is a monoclonal antibody, or a fragment thereof, the monoclonal antibody can be prepared against Bp50 using any technique which provides for the production of antibody molecules by continuous cell lines in culture. For example, the hybridoma technique originally developed by Kohler and Milstein (1975, Nature 256:495-497) as well as other techniques which have more recently become available, such as the human B-cell hybridoma technique (Kozbor et al., 1983, Immunology Today 4:72) and the EBV-hybridoma technique to produce human monoclonal antibodies (Cole et al., 1985, Monoclonal Antibodies and Cancer Therapy, Alan R. Liss, Inc., pp. 77-96) and the like are within the scope of the present invention.

Antibody fragments which contain the idiotype of the molecule could be generated by known techniques. For example, such fragments include but are not limited to: the F(ab')$_2$ fragment which can be generated by treating the antibody molecule with pepsin; the Fab' fragments which can be generated by reducing the disulfide bridges of the F(ab')$_2$ fragment; the F(ab')$_2$ fragment which can be generated by treating the antibody molecule with papain; and the 2Fab or Fab fragments which can be generated by treating the antibody molecule with papain and a reducing agent to reduce the disulfide bridges.

Where the ligand that binds Bp50 is a lymphokine, the lymphokine may be obtained from natural sources or if its amino acid sequence is known or deduced the lymphokine can be synthesized via chemical synthetic methods. Alternatively, if the gene sequence of the lymphokine is known, recombinant DNA techniques may be utilized to clone the gene in an expression vector which provides for transcription and translation of the gene sequence in an appropriate host cell.

Depending upon its intended use, the ligand or appropriate fragments of the ligand may be chemically modified by the attachment of any of a variety of compounds to the ligand using coupling techniques known in the art. Such techniques may include but are not limited to the use of carbodiimide, cyanogen bromide, bifunctional reagents such as glutaraldehyde, N-succinimidyl 3-(2-pyridyldithio) propionate (SPDP), Schiff base reactions, attachment to sulfhydryl moieties, the use of sodium isothiocyanate, or enzymatic linkage, to name but a few. Where a radioisotope is to be attached to the ligand this may also be accomplished via enzymatic means, oxidative substitution, chelation etc. For a review of the chemical reagents which can be used for protein modification see, Lundblad and Noyes, Chemical Reagents for Protein Modification, Volume II, CRC Press, Inc., Boca Raton, Florida, Ch. 5, pp.123-139, 1984.

The chemical linkage or coupling of a compound to the ligand could be directed to a site on the ligand that does not participate in binding to Bp50. This could be accomplished by protecting the binding site of the ligand prior to performing the coupling reaction. For example, the ligand can first be bound to Bp50 in order to protect the Bp50 binding site, then the coupling reaction can be accomplished to link the desired compound to available reactive sites on the ligand-Bp50 complex. Once the coupling reaction is complete, the complex can be disrupted thereby generating a modified ligand to which the desired compound is attached so that the Bp50 binding site of the molecule is minimally affected. Where the ligand comprises a monoclonal antibody such as G28-5, in which the Fc domain of the molecule is not required for the ligand to exert its effect (see Section 5.3.3. infra) it may be advantageous to direct the coupling of desired compounds to the Fc domain of the molecule.

The subsections below describe the new, 50-kDa B-cell surface marker, Bp50, which apparently functions in B-cell proliferation as well as ligands which bind to the new 50 kDa receptor, and their uses. As an example of the ligands of the present invention a monoclonal antibody which defines Bp50 and its F(ab')$_2$ fragments are also described which, like BCGF, augments B-cell proliferation. Unlike anti-Bp35 mAb, which can induce resting B-cells in G$_0$ to enter G$_1$, anti-Bp50 mAb does not activate resting B-cells. Anti-Bp35 and anti-Bp50 mAb together, without any additional exogenous signals, induce strong activation and proliferation of purified B-cells.

The experiments described below also demonstrate that anti-Bp50 activity resembles BCGF activity but that antiBp-50 is distinct from one BCGF since anti-Bp50 and low molecular weight BCGF are clearly additive and act differently on various B-cell subsets or malignancies. Bp50 may be a receptor for a distinct BCGF or for a transmembrane signal that modulates BCGF production or BCGF receptor expression.

5.1. METHODS USED TO CHARACTERIZE THE Bp50 RECEPTOR

Cell preparations

Mononuclear cells were isolated from normal or leukemic hyparanized peripheral blood by Ficoll-Hypaque gradients (Pharmacia, Piscataway, N.J.). Mononuclear cells were obtained from tonsillar tissues as described (Clark, et al., 1985, Proc. Nat. Acad. Sci. U.S.A. 82:1766–1770). T cells were depleted with AET-treated sheep erythrocyte rosetting and Ficoll-Hypaque gradient separation. In some experiments blood B-cells were enriched by isolating nylon wool adherent cells. Monocytes were removed by incubation on plastic petri dishes one or two times at 37° C. for 45 minutes unless otherwise stated. Buoyant or dense tonsillar B-cell fractions were isolated by Percoll step gradients as described (Clark, et al., 1985, Proc. Nat. Acad. Sci. USA 82:1766–1770). Dense tonsillar B-cell preparations consistently had greater than 95% sIg+Bp35+ cells. Blood B-cell-enriched preparations had 60-85% sIg+ cells. B-cell lymphoma cells were isolated by gently teasing lymphoma cells into medium followed by Ficoll-Hypaque gradient centrifugation.

Monoclonal antibodies. The G28-5 antibody to Bp50 was generated by immunizing BALB/c mice with human E- tonsillar lymphocytes and fusing immune spleen cells with the NS-1 myeloma (Kohler, et al., 1975, Nature 256:495-497; Ledbetter, et al., 1979, Immunol. Rev. 47:63-82). Hybrid cell cultures secreting antibody reactive with tonsillar B-cells and not with T cells were identified by the use of indirect immunofluorescence (IF) and analysis with a FACS IV cell sorter; cultures with antibody giving histogram patterns similar to known mAb to pan B-cell markers (e.g., Bp35) were cloned and selected for further study. The G28-5 clone produced an $IgG_1$ mAb that reacted only with normal or malignant B-cells or B-cell lines. Other mAb used in this study have been described in detail (Clark, et al., 1985, Proc. Nat. Acad. Sci. USA 82:1766-1770; Clark et al., 1986, Human Immunol. 16:100; Ledbetter, et al., 1986, Human Immunol.15:30-44; Ledbetter, et al., 1985, in *Perspectives in Immunogenetics and Histocompatibility*, ASHI, New York, 6, pp. 325-340). These include IF5 ($IgG_{2a}$) anti-Bp35, HB10a ($IgG_{2a}$), anti-HLA-DR, 2C3 ($IgG_1$) anti-u chain, G19-4 ($IgG_1$) anti-CD3, FC-2 ($IgG_{2a}$) anti-Fc receptor CD16, and 9.6 ($IgG_{2a}$) anti-CD2 (E receptor) provided by Dr. Paul Martin (Martin, et al., 1983, J. Immunol. 131:180). The $IgG_1$ mAbs were purified by precipitation using 45% or 50% saturated ammonium sulfate and DEAE Sephacryl column chromatography, and the $IgG_{2a}$ mAbs were purified by the use of protein A Sepharose columns. The F(ab')2 fragments of G28-5 were prepared by the method of Parham (Parham, et al., 1983, J. Immunol. 131:2895) purified on a 2-meter long sephacryl S200 column, and assayed for purity by SDS-PAGE (Ledbetter, et al., 1985, J. Immunol. 135:1819). The 2C3 mAb to u-chains was conjugated to Sepharose 4B beads (Pharmacia Fine Chemicals, Uppsala, Sweden) using cyanogen bromide coupling.

Fluorescein and phycoerythrin conjugations. Purified mAb were either directly conjugated with fluorescein using fluorescein-isothiocyanate (FITC; Molecular Probes) (green) by the method of Goding (Goding, et al., 1976, J. Immunol. Meth. 13:215-226), or conjugated to R-phycoerythrin (PE) (red) by using SPDP (Pharmacia) with a method we have detailed in Ledbetter, et al., 1985, in *Perspectives in Immunogenetics and Histocompatibiity*, ASHI, New York, 6, 119-129. Lymphoid cells were incubated in round-bottom microtiter plates for 30 minutes with an appropriate dilution of green and/or red mAb, washed twice, and then analyzed on a FACS IV cell sorter.

Two-color immunofluorescence. Two-color studies were done with a fluorescence-activated cell sorter (FACS IV: Becton-Dickinson, Mountain View, CA) by using a 560-nm dichroic mirror to split the beam and a 580 long-pass filter and a 540 short-pass filter (Ditric Optics, Hudson, Mass.) in front of the red and green photomultiplier tubes, respectively. In addition, a two-color compensator (T. Nozaki, Stanford University) was used to correct for minor spillover of green and red signals. For each two-color stain, data from 40,000 cells were collected and stored on floppy disks. Data are presented as cell number (vertical) versus log green fluorescence versus log red fluorescence on a $64 \times 64$ dot grid. Approximately 4.5 dots represents a doubling of fluorescence. Unstained cells are positioned at the back corner of the grid; red fluorescence is to the right and green fluorescence is to the left. Our flow cytometry system for two-color IF with fluorescein and phycoerythrin is described in more detail (Ledbetter, et al., 1985, in *Perspectives in Immunogenetics and Histocompatibiity, ASHI*, New York, 6, 119-129 and 325-340).

Cell culture. Blood or tonsillar lymphoid cells were cultured at $5-10 \times 10^5$ ml in quadruplicate in 96-well microtiter plates containing 200 ul RPMl-1640 medium supplemented with 15% fetal bovine serum, antibiotics, glutamine, and pyruvate (R15). After 1 to 7 days, cells were pulsed with 0.5 uCi of $^3$H thymidine per well (New England Nuclear, 6.7 Ci/mmol; 1 Ci=37) for 18 hours. Cells were then harvested onto glass-fiber filters with a cell harvester, and radioactivity was measured in a scintillation counter. In some experiments, antibodies or factors were added at various times after the start of cultures; proliferation in these experiments was measured on day 3.

Costimulatory factors. Purified BCGF was purchased from Cytokine Technology (Buffalo, New York) and contained no detectable IL-1, IL-2, or interferon activity. This BCGF was prepared by the method of Maizel and coworkers (Maizel, et al., 1982, Proc. Nat. Acad. Sci. USA 79:5998), who have shown that the major BCGF activity in this material resides in a 12-kDa species, hereinafter referred to as "BCGF (low)" (Mehta, et al., 1985, J. Immunol. 135:3298). The purification steps included preparative scale DEAE affinity chromatography followed by hydroxylapatite column chromatography. IL-1 purified to homogeneity was the generous gift of Dr. Steven Dower (Dower, et al., 1985, J. Exp. Med. 162:501). Recombinant IL-2 was kindly provided by Cetus Corporation. TPA (12-0-tetradeconoyl phorbol 13-acetate) was purchased from Sigma.

Detection of cell activation. Changes in cell volume induced by mAb and/or factors were measured using a cell sorter and forward angle light-scatter. Cell cycle changes in cellular RNA and DNA levels were measured by staining activated cells with acridine orange and measuring relative cellular RNA (red) and DNA (green) content with a cell sorter by the method of Darzynkiewicz et al. (Darzynkiewicz, et al., 1980, Proc. Nat. Acad. Sci. USA 77:6697-6702). Changes in relative levels of cell surface antigens were monitored by use of mAb directly conjugated with fluorescein and then quantitated by direct IF fluorescence levels with an Epics V cell sorter.

Biochemical characterization of Bp50. Immunoprecipitation of Bp50 from surface $^{125}$I-labeled tonsillar cells was performed as described (Ledbetter, et al., 1985, J. Immunol. 134:4250-4254). Isolated antigens were electrophoresed on 10% SDS polyacrylamide slab gels without reduction. Gels were visualized using autoradiography at −70° C. and Cronex lightening plus intensifying screens (Dupont).

5.2. CHARACTERIZATION OF THE Bp50 RECEPTOR

The subsections below describe the results of the experiments conducted using the methods described above.

5.2.1. IDENTIFICATION OF A B-CELL SPECIFIC 50 kDA CELL SURFACE MARKER, Bp50.

A mAb to Bp50 was raised by immunizing BALB/c mice with human tonsillar lymphocytes and fusing immune spleen cells with the NS-1 myeloma. One clone, G28-5, produced an IgG$_1$ mAb that did not contain the NS-1 light chain. Upon scrutiny by IF analysis, G28-5 was found to react only with normal or malignant B-cells or B-cell lines. A comprehensive screening of normal tissues by established methods (Clark, et al., 1985, Proc. Nat. Acad. Sci. USA 82:1766-1770; Ledbetter et al., 1986, Human Immunol.15:30-44; Ledbetter, 1985, in *Perspectives in Immunogenetics and Histocompatibility*, ASHI, New York, 6, pp. 325-340) revealed that the G28-5 antibody reacts with E rosette negative (Er-) cells from blood or tonsils but not with nylon wool nonadherent T cells, PHA-induced T-cell blasts, or with blood granulocytes, monocytes, red cells, or platelets. It reacted strongly with all seven B lymphoblastoid cell lines tested and with three Burkitt's lymphoma lines (Raji, Daudi, Namalwa), but not with four T cell lines (CEM, HSB-2, JURKAT, and HPB-ALL). All chronic lymphocytic leukemias tested (3/3) and 90% (9/10) of B lymphomas tested expressed the Bp50 marker while only 28% (2/7) of non T, non B CALLA+ acute lymphocytic leukemias expressed Bp50.

The restricted distribution of Bp50 on normal tissues was further confirmed by quantitative two-color immunofluorescense (two color IF) analyses. Using an R-phycoerythrin (PE)-conjugated antibody (red) to the pan B-cell antigen Bp35 (B1, CD20) and fluorescein-conjugated anti-Bp50 antibody (green), we found that Bp50 was expressed only on Bp35+ B-cells (FIG. 1) in blood or tonsils. Blood B-cells consistently expressed somewhat lower levels of Bp50 than tonsillar B-cells; this is similar to HLA-DR expression, (Ledbetter et al., 1986, Human Immunol.15:30-44) and to gp54 expression (Wang, et al., 1979, J. Exp. Med. 149:1424-1433) which are also lower on blood B-cells. Bp50 was expressed at similar levels on tonsillar B-cell subpopulations separated on Percoll gradients into buoyant and dense fractions. Using our PE-conjugated mAb to the T cell marker, CD3(T3), and NK cell-associated marker, CD16(Fc receptor) (Ledbetter, et al., 1979, Immunol. Rev. 47:63-82), we found that Bp50 is not expressed on T cells or NK cells. Using two-color IF, we also found that CD3+ PHA blasts that expressed high levels of IL-2 receptors did not express BP50.

Figure 2A:
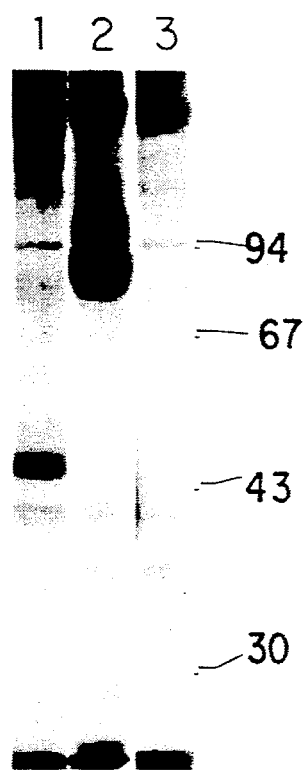
Figure 2B:
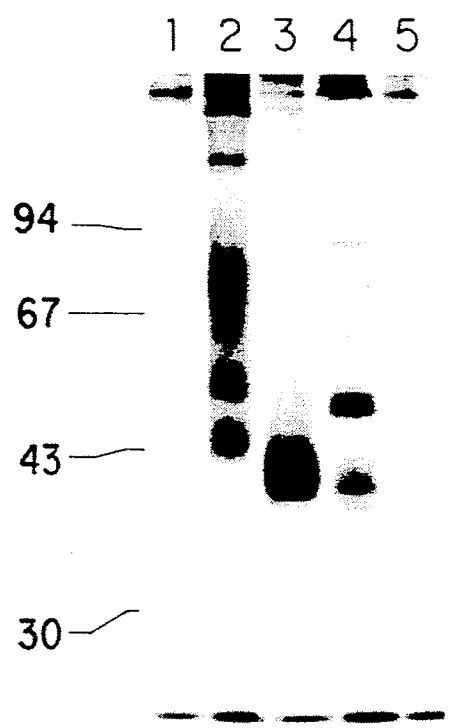

The G28-5 antibody reacted with a single polypeptide on tonsillar lymphocytes that migrated at approximately 50 Kd under non-reducing conditions (FIG. 2A). This molecule is larger than previously reported B-cell markers in the same molecular weight range such as Bp39 or Bp45 (Zipf, et al., 1983, J. Immunol. 131:3064-3072; Kitner, et al., 1981, Nature 294, 458-460; Clark, et al., 1986, in *Leukocyte Typing II*, eds. Reinherz, et al., Springer Verlag, Berlin, Chap. 12 Vol. 2, 155-167; Slovin, et al., 1982, Proc. Nat. Acad. Sci. USA 79:2649-2653; Thorley-Lawson, et al., 1985, J. Immunol. 134:3007-3012, and FIG. 2B). The exposure time for this gel was selected so that the molecular weights of the other B-cell markers could be readily compared with Bp50. The Bp39 marker, unlike Bp50, is expressed on granulocytes and Bp45, unlike Bp50, is restricted to B-cell blasts. Antibodies to Bp39 (41-H16) and Bp45 (MNM6, Blast-1, Blast-2) made available through an international workshop (Clark, et al., 1986, in *Leukocyte Typing II*, eds. Reinherz, et al., Springer Verlag, Berlin, Chap. 12 Vol. 2, 155-167) did not block the binding of fluoresceinated anti-Bp50 antibodies to B-cells. Thus, based on tissue distribution, biochemical analysis, and blocking studies, the G28-5 monoclonal antibody recognizes a 50-Kd structure distinct from other known B-cell antigens.

5.2.2. EXPRESSION OF Bp50 IS RESTRICTED TO B-CELLS

Both hematopoietic tissue and cell-line distribution studies and detailed two-color flow cytometric analyses revealed that Bp50 is expressed only on B lymphocytes. As illustrated in FIG. 3, Bp50 is expressed on a small subset of blood lymphocytes and on a large population of tonsillar lymphocytes. Virtually all Bp50+cells in both blood and tonsils also expressed Bp35 and HLA-DR, but did not express the CD2 (FIG. 1) or CD3, T-cell molecules or the IgG Fc receptors that are found on NK cells. Furthermore, ConA-activated CD3+ T-cell blasts expressed IL-2 receptors but did not express Bp50.

Two-color flow cytometric analyses allow the quantitative measurement of the density relationship between two surface antigens. We previously showed that the dense, resting B-cells in the mantle zone of secondary follicles express IgM and low levels of Bp35, whereas the buoyant, activated B-cells in the germinal center are IgM-negative and express elevated levels of Bp35 (Ledbetter, et al., Human Immunol. 15:30). FIG. 3 shows that both IgM-positive and IgM-negative B-cell subsets expressed Bp50 in equal amounts, indicating that Bp50 is expressed on both resting B-cells and B-cells activated in vivo.

5 3. AUGMENTATION OF B-CELL PROLIFERATION WITH ANTI-Bp50 ANTIBODY

As previously explained, B-cells can be activated with low doses of anti-u chain specific antibodies. We recently found that the B-cell-specific marker Bp35 (B1), a 35-kDa polypeptide, may also function in early B-cell activation: the IF5 mAb to Bp35, like low doses of anti-u antibody, activates B-cells to increase in cell volume and RNA content and to become responsive to BCGF (Clark, et al., 1985, Proc. Nat. Acad. Sci. USA 82:1766-1770; Gollay, et al., 1985, J. Immunol. 135:3795-3801). Therefore, it was of interest to compare the effect of anti-Bp50 mAb in the proliferation of untreated B-cells or B-cells activated with either anti-Bp35 or anti-u antibodies (Table 1). Anti-Bp35 in solution or anti-u antibodies attached to Sepharose beads, under appropriate conditions alone, could stimulate some B-cell proliferation (Table 1, line 1); in contrast, anti-Bp50 antibodies alone did not stimulate proliferation (Table 1, line 2). However, anti-Bp50 mAb augmented proliferation considerably when cultured with anti-u beads or with anti-Bp35. In this respect anti-Bp50 resembled BCGF (Table 1, line 3). Thus, it was important to determine whether anti-Bp50 and BCGF together could induce B-cell proliferation. As illustrated in Table 1, line 4, anti-Bp50 and BCGF together induced no proliferation, but did augment proliferation of either anti-u or anti-Bp35 activated cells somewhat more than either stimulant alone. BCGF over a three-log range, when used with anti-Bp50 without other signals, had no effect on proliferation of dense B-cells even when anti-Bp50 was used at doses ranging from 0.1 to 10 ug/ml.

TABLE 1

Augmentation of Anti-Ig or Anti-Bp35
Induced B Cell Proliferation With Anti-Bp50 Antibodies Mean Proliferation ± S.E. of B Cells Cultured With:

| Line | Co-stimulant | Media | Anti-u-beads | Anti-Bp35 |
|---|---|---|---|---|
| 1 | None | 1,212 ± 547 | 10,219 ± 462 | 5,539 ± 308 |
| 2 | Anti-Bp50 | 719 ± 718 | 38,792 ± 1,329 | 25,465 ± 616 |
| 3 | BCGF | 456 ± 217 | 14,217 ± 445 | 9,443 ± 343 |
| 4 | Anti-Bp50 + BCGF | 1,456 ± 126 | 54,393 ± 2,537 | 46,488 ± 3,387 |

Proliferation of dense Er- tonsillar B-cells (95% surface IgM⁻ cells) was measured on day 3 as described. Briefly, $2 \times 10^5$ cells/200 ul well were cultured in quadruplicate for 48 hrs with RPMI 1640 medium containing 15% fetal bovine serum plus additives without antibody or with either 2C3 monoclonal antibody to u chains coupled to sepharose beads ("anti-u beads," 50 ug/ml) or free IF5 anti-Bp35 antibody (5 ug/ml). Cultures containing media, "anti- u beads," or anti-Bp35 were cultured alone or with BCGF (5% final concentration, Cytokine Technology, Buffalo, New York; has no detectable IL-1 or IL-2 activity), with anti-Bp50 (1:1000 dilution of ascites) as co-stimulants. After 40 hrs cells were pulsed with $^3$H-thymidine, and counts incorporated were measured after 18 hrs.

5.3.1. ANTI-Bp50 mAb AUGMENTS PROLIFERATION ONLY AFTER B-CELLS ARE ACTIVIATED BY ANTI-Bp35 OR ANTI-u-ANTIBODIES

The results in Table 1 suggest that anti-Bp50 mAb could not induce proliferation by itself. As shown in FIG. 4, doses of anti-Bp50 ranging from 0.05 ug to 2.0 ug/ml had no effect on $^3$H-thymidine uptake. However, in the presence of optimal levels of anti-Bp35 mAb, as little as 0.1 to 0.5 ug/ml of anti-Bp50 antibodies augmented proliferation substantially. As much as 50,000 to 70,000 cpm were detectable at the optimal time of proliferation when highly purified B-cells were cultured only with anti-Bp35 plus anti-Bp50. A consistent observation was that higher doses of anti-Bp50 (greater than 2-5 ug/ml) were less effective than doses in the 100-200 ng range.

These results suggested that anti-Bp50 may function only after B-cells are activated by other signals. Data shown in FIG. 5 suggest that this is indeed the case. If B-cells were first activated with anti-Bp35, anti-Bp50 could be added as late as 24-48 hours later and still augment proliferation at day 4. In contrast, when cells were first treated with anti-Bp50, anti-Bp35 was effective only if added within a few hours after the start of cultures. Similar results were found when anti-u rather than anti-Bp35 was used.

5.3.2. ANTI-Bp50 mAb DO NOT ACTIVATE B-CELLS OUT OF G₀ BUT DO INDUCE ACTIVATED B-CELLS TO PROGRESS THROUGH THE CELL CYCLE

Figure 6A:
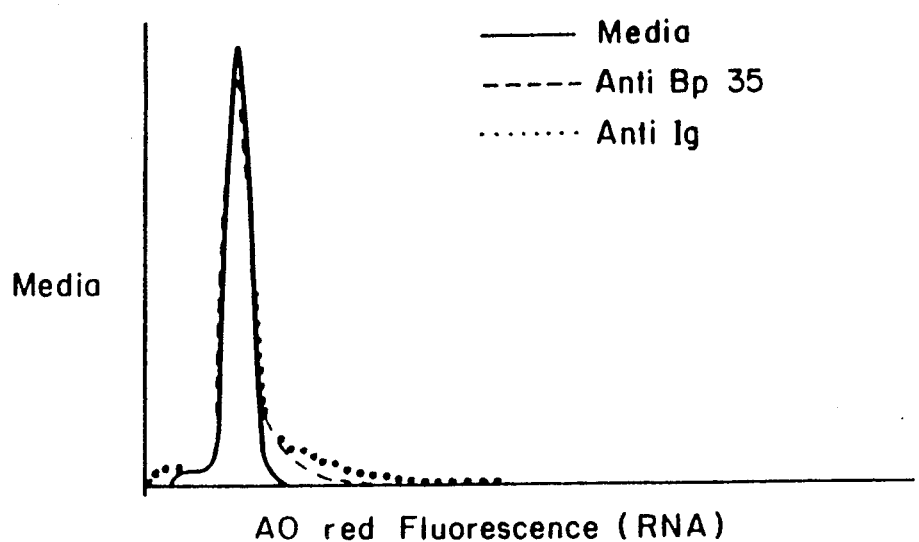
Figure 6B:
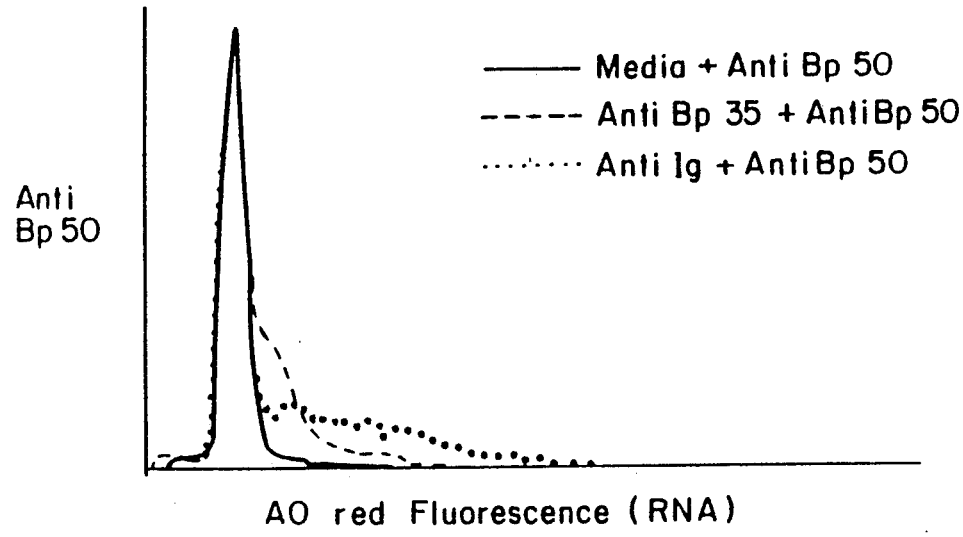

Previously, we have found that anti-Bp35, like low doses of anti-u antibodies, induce resting tonsillar B-cells in $G_0$ to enlarge (Clark, et al., 1986, Leukocyte Typing II, eds., Reinherz, et al., Springer Verlag, Berlin, Vol. 2, 455-462) and to enter the $G_1$ phase of the cell cycle (Gollay, et al., 1985, J. Immunol. 135:3795-3801). Thus, it was of interest to compare the ability of anti-Bp50 mAb to anti-Bp35 mAb for their effects on B-cell activation. As shown in FIG. 6A, unstimulated dense tonsillar B-cells even after 3 to 4 days in culture had a uniform RNA profile characteristic of cells in $G_0$ (Darzynkiewicz, 1980, Proc. Nat. Acad. Sci. USA 77:6697-6702). However, about 15-30% of cells stimulated with anti-Bp35 or anti-u had increased RNA content indicative of entry into $G_1$. In contrast, neither anti-Bp50 (FIG. 6B) nor BCGF (FIG. 6C) alone induced significant numbers of B-cells to enter $G_1$. For instance, 2 days after activation, anti-Bp35 and anti-Ig mAb induced respectively 13.5% and 20.9% of tonsillar cells to enter $G_1$, whereas cells treated with only anti-Bp50 (2.7%) or BCGF (3.2%) remained at media control levels (2.2%). However, when either anti-Bp50 or BCGF were added together with anti-Bp35 or anti-u antibodies, the proportion of cells entering $G_1$ increased dramatically. Similarly, anti-Bp50 and BCGF alone did not induce B-cells to enter S phase (Table 2), but together with either anti-Bp35 or anti-u did increase the number of S phase cells two- to threefold.

TABLE 2

Effect of Anti-Bp50 and BCGF on
Cell Cycle Progression in Tonsillar Lymphocytes

| Competence Signal | Progression Signal | % Cells $G_0$ | $G_1$ | S/$G_2$/M |
|---|---|---|---|---|
| media | none | 89.9 | 7.1 | 2.5 |
| anti-Bp35 | " | 80.4 | 14.5 | 3.7 |
| anti-Ig | " | 65.6 | 27.6 | 5.7 |
| media | anti-Bp50 | 83.6 | 12.0 | 3.3 |
| anti-Bp35 | " | 54.1 | 35.5 | 9.7 |
| anti-Ig | " | 43.6 | 36.2 | 16.2 |
| media | BCGF | 85.4 | 11.7 | 2.2 |
| anti-Bp35 | " | 56.6 | 32.6 | 11.6 |
| anti-Ig | " | 48.4 | 36.1 | 14.1 |

Percentage of cells in $G_0$, $G_1$, or S and $G_2$ determined with the use of the acridine orange-staining procedure (Darzynkiewicz, et al., 1980 Proc. Nat. Acad. Sci. USA 77:6697-6702); $1 \times 10^6$ dense tonsillar lymphocytes with anti-Bp35 (5 ug/ml), anti-u on beads (50 ug/ml), anti-Bp50 (0.4 ug/ml), BCGF (5%) or combinations as shown.

5.3.3. OPTIMAL CONDITIONS FOR AUGMENTING B-CELL PROLIFERATION WITH ANTI-Bp50 ANTIBODIES

Antibodies to Bp50 by themselves have little or no detectable effect on dense resting B-cells (Table 3). However, in the presence of agents that can activate B-cells, such as anti-Ig, anti-Bp35 and TPA, anti-Bp50 mAb clearly augmented proliferation. Anti-Bp50 did not costimulate with several interleukins, including purified IL-1, recombinant IL-2 and BCGF (low). A comparison of the effects of anti-Bp50 with those of BCGF (low) showed that the same agents that were costimulatory with anti-Bp50 were also costimulatory with BCGF (low) (Table 3). Of particular interest was the finding that together BCGF and anti-Bp50 still were not costimulatory for resting cells.

TABLE 3

Augmentation of B-Cell Proliferation with Anti-Bp50 Antibodies or B-Cell Growth Factor

| | Mean Proliferation ± S.E. of B-Cells Cultured with: | | |
|---|---|---|---|
| Co-stimulant | Media | Anti-Bp50 (200 ng/ml) | BCGF (5%) |
| none | 96 ± 1 | 267 ± 15 | 285 ± 74 |
| anti-Ig | 5,833 ± 391 | 41,634 ± 2,103 | 25,094 ± 61 |
| anti-Bp35 (5 ug/ml) | 457 ± 45 | 8,143 ± 280 | 1,733 ± 32 |
| TPA (2 ng/ml) | 7,361 ± 537 | 21,163 ± 871 | 13,064 ± 1,030 |
| IL-1 (10 U/ml) | 264 ± 2 | 308 ± 23 | 221 ± 8 |
| IL-2 (100 U/ml) | 204 ± 34 | 350 ± 7 | 220 ± 11 |
| BCGF (5%) | 220 ± 7 | 851 ± 28 | 270 ± 18 |

Dense Er- tonsillar B-cells (greater than 95% sIgM$^-$ cells) cultured for 48 hr at 2 × 10$^5$ cells/well followed by 24 hr pulse with $^3$H-thymidine before counting.

The kinetics of proliferation augmented by anti-Bp50 is shown in FIG. 7. The peak of proliferation occurred at day 4 and then waned whether or not cells were activated with anti-Bp35 or other activators such as anti-Ig or TPA. The kinetics of proliferation augmented by BCGF or by anti-Bp50 were similar.

As little as 0.05 ug of anti-Bp50 antibodies augmented proliferation. An optimal dose of 0.3 ug/ml was used in subsequent studies. A consistent observation was that when using whole antibody molecules, higher doses of anti-Bp50 (greater than 2-5 ug/ml) were less effective than doses in the 0.1-0.5 ug/ml range.

Human B-cells are exquisitely sensitive to inhibitory effects mediated by the Fc receptors of antibodies binding to surface Ig (Parker, 1980, Immunol. Rev. 52:115; Bijsterbosch, et al., 1985, J. Exp. Med. 162:1825). Thus, it was important to compare the efficacy of whole anti-Bp50 mAb with that of anti-Bp50 F(ab')$_2$ fragments. Over a 100-fold dose range F(ab')$_2$ fragments were clearly as effective as, or more effective than, whole antibody at augmenting B-cell proliferation (Table 4). Thus, the Fc domain of anti-Bp50 mAb is not required for anti-Bp50 to exert its effect and, if anything, may be inhibitory. In other words, anti-Bp50, like BCGF, apparently can act as a soluble mediator without the aid of Fc receptor-mediated accessory cell function.

TABLE 4

The Fc Domain of Anti-Bp50 Antibodies is Not Required for Augmenting B-Cell Proliferation

| | | Mean Proliferation of B Cells Cultured with: | |
|---|---|---|---|
| Anti-Bp50 | Dose (ug/ml) | Media | Anti-Bp35 |
| none | — | 295 ± 16 | 269 ± 27 |
| whole Ab | 0.125 | 278 ± 32 | 5,140 ± 20 |
| | 1.25 | 275 ± 24 | 4,686 ± 342 |
| | 12.5 | 163 ± 15 | 3,852 ± 203 |
| F(ab')$_2$ | 0.125 | 594 ± 21 | 10,635 ± 449 |
| | 1.25 | 531 ± 3 | 10,893 ± 575 |
| | 12.5 | 279 ± 8 | 9,411 ± 870 |

Cell culture conditions were as described in Table 3.

5.3.4 DIFFERENCES BETWEEN ANTI-Bp50 AND BCGF (LOW) ACTIVITY

Figure 8A:
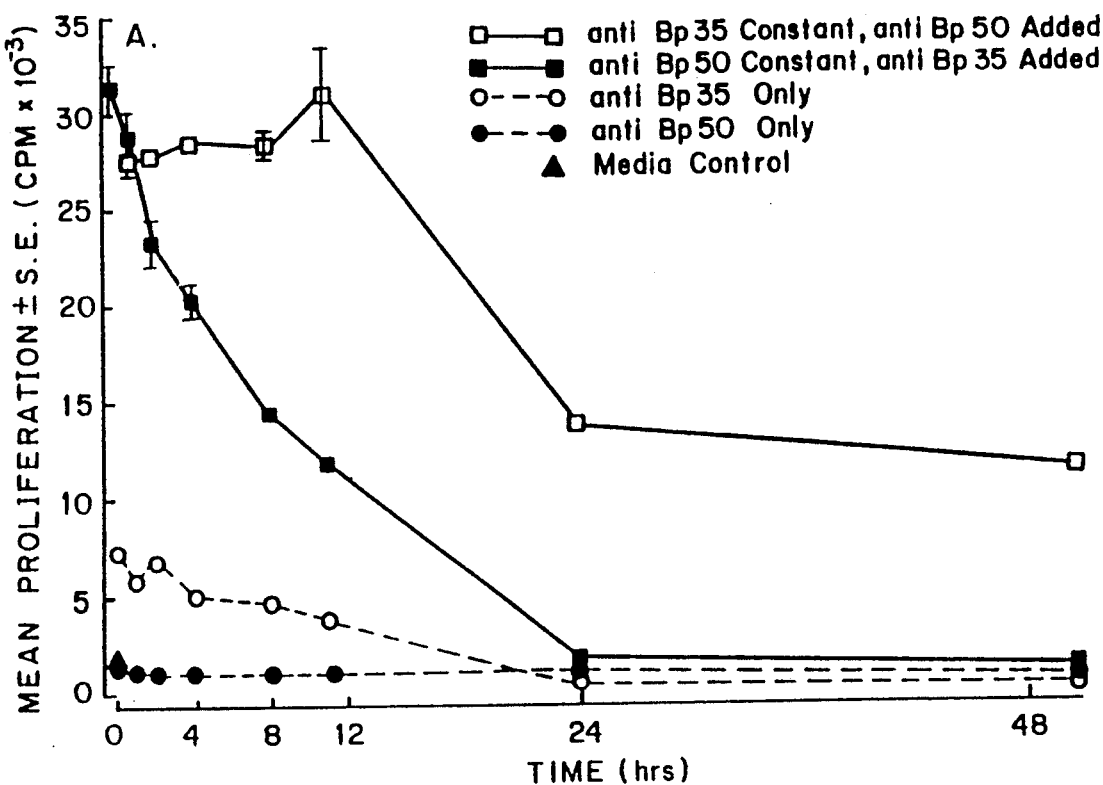
Figure 8B:
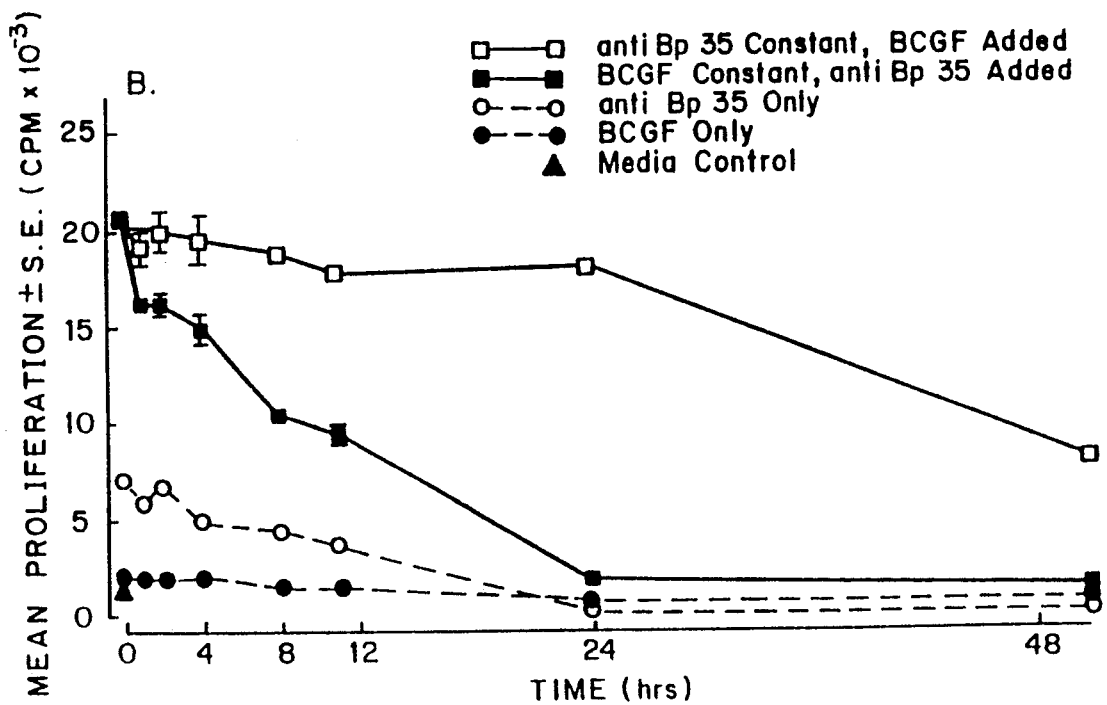

Anti-Bp50 and BCGF (low) had a similar effect on B-cells and were costimulatory with the same agents (Table 3). However, several lines of evidence indicate that anti-Bp50 and the BCGF used in this study apparently operate through different signals. First, Bp50 molecules, unlike BCGF (low) receptors (Bijsterbosch, et al., 1985, J. Exp. Med. 162: 1825), are expressed on resting blood B-cells (FIG. 3). Second, although both anti-Bp50 and BCGF (low) function most effectively when added after anti-Bp35 or anti-Ig, anti-Bp50 clearly was optimally effective when added 12 hours after cultures began (FIG. 8A). In contrast, BCGF (low) could be added as long as 24 hours after start of cultures and still optimally augment proliferation (FIG. 8B). These kinetic experiments, which are modeled after the approach of Howard and Paul (1983, Ann. Rev. Immunol. 1:307), suggest that a Bp50-dependent signal may normally exert its effect before BCGF.

Both anti-Bp50 and BCGF (low) augmented proliferation of B-cells activated with anti-Bp35 or anti-Ig (Table 3). However, the effect of anti-Bp50 and BCGF (low) were additive in many experiments (FIG. 7). FIG. 9 shows a titration of BCGF (low) in an experiment where anti-Bp50 was used at its optimal concentration (0.2 ug/ml). BCGF (low) could further augment proliferation of resting B-cells in the presence of anti-Bp50 after activation by either anti-Ig or by anti-Bp35. Optimal concentrations of BCGF (low) were 5-10%, while 25% was inhibitory. Thus, when anti-Bp50 and BCGF (low) were both used at their optimal concentrations, they still showed additive effects on B-cell proliferation.

Figure 10A:
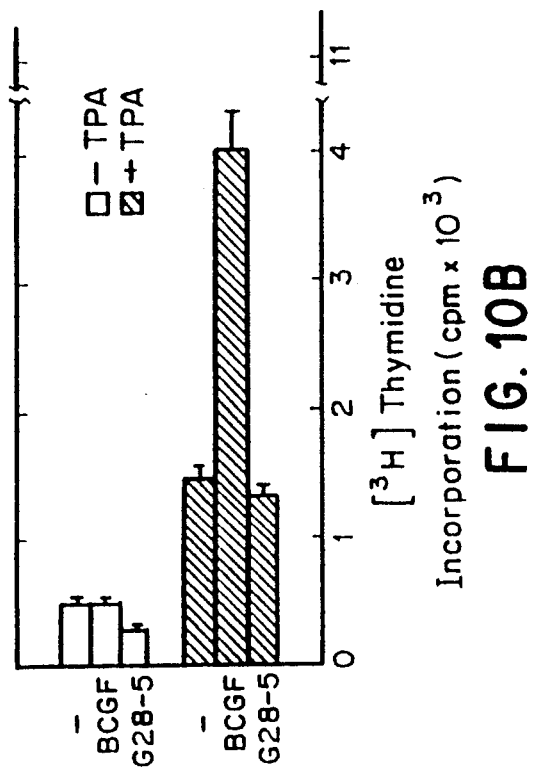
Figure 10B:
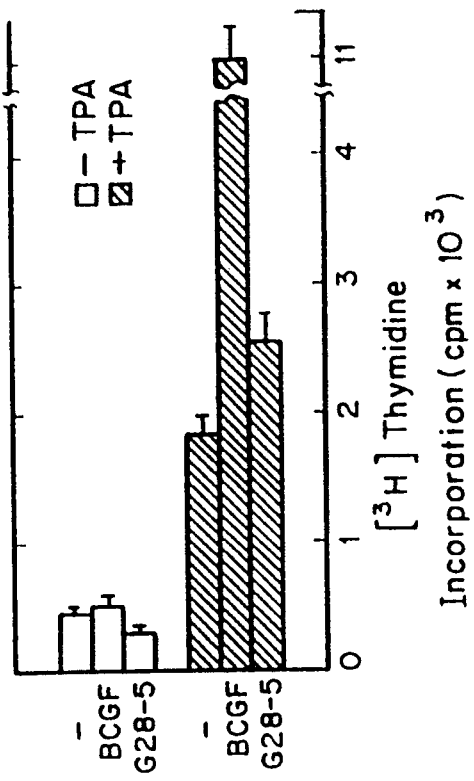
Figure 10C:
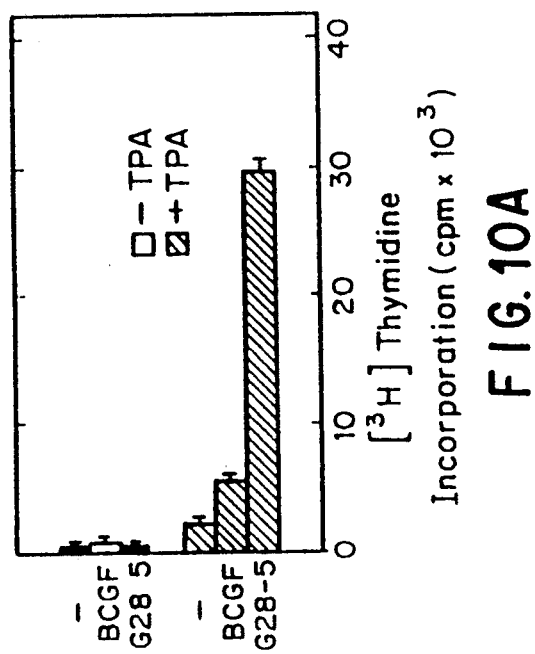
Figure 10D:
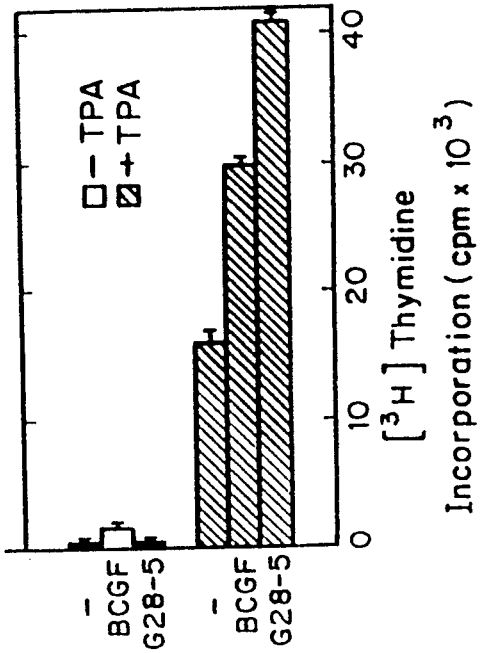

Finally, both normal and malignant B-cell subsets differed in their responses to anti-Bp50 and to BCGF (low). For example, some blood B-cells responded to BCGF (low) but did not respond to anti-Bp50 (Table 5). An additional activation signal such as anti-Bp35 (Table 5) or TPA (FIG. 10) was consistently necessary to allow blood B-cells to respond to anti-Bp50. While dense tonsillar B-cells generally did not respond to either BCGF or anti-Bp50, buoyant B-cells did respond (Table 5). B-cell malignancies also differed in their responsiveness to anti-Bp50 versus BCGF. For example, some B-cell lymphomas responded to TPA plus BCGF (low) but not to TPA plus G28-5 anti-Bp50 (FIG. 10B and D). In contrast, dense tonsillar B-cells and peripheral blood B-cells responded to TPA plus either BCGF (low) or anti-Bp50 (FIG. 10A and C).

TABLE 5
B-Cell Subsets Differ in Their Responsiveness to Anti-Bp50 or BCGF

| | Mean Proliferation(± S.E.M.) of Lymphocytes From | | | | |
|---|---|---|---|---|---|
| | Blood | | | Tonsils | |
| Stimulation | Exp 1 | Exp 2 | Exp 3 | Dense | Buoyant |
| none | 527 ± 70 | 659 ± 133 | 906 ± 106 | 385 ± 43 | 387 ± 12 |
| BCGF (5%) | 13,918 ± 1,082 | 37,594 ± 2,023 | 3,347 ± 174 | 332 ± 33 | 1,451 ± 57 |
| anti-Bp50 (0.5 ug/ml) | 519 ± 28 | 1,013 ± 81 | 1,151 ± 28 | 472 ± 8 | 1,543 ± 20 |
| anti-Bp35 (5 ug/ml) | 554 ± 90 | 645 ± 89 | 665 ± 115 | 2,415 ± 80 | 1,129 ± 68 |
| anti-Bp50 + anti-Bp35 | — | 12,274 ± 546 | 15,667 ± 333 | 36,589 ± 1,335 | 4,843 ±0 136 |
| anti-Bp50 + BCGF | — | — | 3,943 ± 115 | 1,342 ± 19 | 2,899 ± 91 |

Cell culture conditins as described in Table 1. Blood Nylon wood adherent lymphocytes (B cells plus monocytes) were depleted of monocytes by incubation on plastic dishes overnight prior to stimulation (Exp. 1 and Exp. 2). In Exp. 3, blood E-lymphocytes were depleted of monocytes by incubation on plastic dishes for 1 hr. prior to stimulation. Tonsillar $E_r$-lymphocytes were fractionated using Percoll gradients into dense (pellet) or buoyant (fraction 1) subsets (32).

5.4. USES OF ANTI-Bp50 LIGANDS AND Bp50

The ligands of the present invention may be used in vivo or in vitro, in their unmodified or modified forms to modulate immune responses. For example, the ligands themselves may be used as an "adjuvant" to increase an immune response to a vaccine or to increase the immune response of an immunosuppressed individual. Alternatively, if cytotoxins or anti-proliferative agents are coupled to the ligands, these modified ligands may be used to decrease an immune response, for example, in autoimmune disease or in transplant patients to obviate graft rejection. These modified ligands could also be used to treat malignancies that comprise cells or tumors which express the Bp50 antigen whether or not the malignancy is B-cell in origin.

Both the ligands of the present invention and/or Bp50 itself can be used in vitro. Such applications include in vitro assays, such as immunoassays for the detection of cells which express the Bp50 antigen and/or for the detection of shed Bp50 antigen, if any, in body fluids. In this instance the ligand or Bp50 could be labeled with a radiolabel, fluor, enzyme, enzyme substrate, dye, etc. In addition, the ligands may be used to separate and/or identify cells which express the Bp50 antigen, in which case the ligand may be coupled to an immobile support, or to a fluor which can be used in a FACS (fluorescence activated cell sorter).

The various applications and uses of the ligands and Bp50 of the present invention are discussed in more detail below.

5.4.1. Bp50 RECEPTOR AND USES OF LIGANDS SUCH AS ANTI-Bp50 TO AUGMENT B-CELL PROLIFERATION

Previous studies have suggested that the factors involved in the induction of B-cells from $G_0$ into the $G_1$ phase of the cell cycle are distinct from the factors or requirements for transit into the S phase. This model is based principally on studies showing that agents such as low doses of anti-Ig B-cell activation factors, or anti-Bp35 alone have little or no effect on B-cell proliferation. Yet, these same agents can drive B-cells to a point in cell activation where they are susceptible to growth factors. In contrast, growth factors such as BCGF or IL-2 alone have no effect on resting B-cells but do augment growth of activated B-cells.

While the present invention is not to be limited to any theory or explanation, the results presented herein provide additional support for a model of distinct regulation of B-cell activation and growth steps. Here we have shown that activation and proliferation signals in human B-cells may be transmitted through distinct cell surface structures. Although anti-Bp35 mAb activated B-cells to enter the $G_1$ phase of the cell cycle, alone, it induced little or no proliferation. Anti-Bp50 mAb had the opposite effect: it could not activate B-cells, but when added even as late as 12-24 hours after activation could induce B-cell growth.

The Bp50 molecule presumably could normally function as either a receptor for a ligand such as a soluble growth factor or for a signal mediated through cell-cell contact (i.e., a ligand found on the surface of another cell). Previous studies have identified several T cell-derived BCGFs that, like anti-Bp50, augment B-cell proliferation. Both high and low molecular weight forms of B-cell growth factors have been identified and different types have been shown to have additive effects (Kehrl, et al., 1984, Immunol. Rev. 18:75-96; Kishimoto, 1985, Ann. Rev. Immunol. 3:133-157; Swain, et al. 1983, J. Exp. Med. 158:822-835; Howard et al., 1984, Immunol. Rev. 78:185-210; Ambrus, et al., J. Clin. Invest. 75:732-739; Ambrus, 1985, J. Exp. Med. 162:1319-1335). Thus, Bp50 might be a receptor for one of these factors.

With the exception of IL-2 receptors and the C3d receptor, the receptors on B-cells for growth signals have not yet been identified. The mAb AB-1 reacts with a B-cell marker expressed only on activated B-cells and blocks BCGF-dependent proliferation, and thus might recognize the BCGF receptor or a related structure. Bp50 appears to be distinct from the AB-1 marker since the AB-1 mAb does not block the binding of the G28-5 anti-Bp50 antibody, and unlike the G28-5 mAb, reacts only with activated B-cells (Jung, et al., 1984, J. Exp. Med. 160:1919-1924). Bp50 is on all B-cells, which based on absorption analysis and direct binding assays appears not to be the case for BCGF receptors. Our current data indicate that Bp50 and the receptor for low molecular weight BCGF are distinct structures. Using a rabbit heteroantiserum, Wang and coworkers (Wang, 1979, J. Exp. Med. 149:1424-1433) previously described a 54-kDa glycoprotein, gp54, that like Bp50 is expressed on all B-cells but at lower levels on blood B-cells than tonsillar B-cells. It is possible, but unlikely, that the rabbit heteroantiserum and anti-Bp50 recognize the same or related structures: unlike anti-Bp50 mAb, the rabbit antiserum to gp54 alone was sufficient to stimulate B-cell proliferation.

Figure 6C:
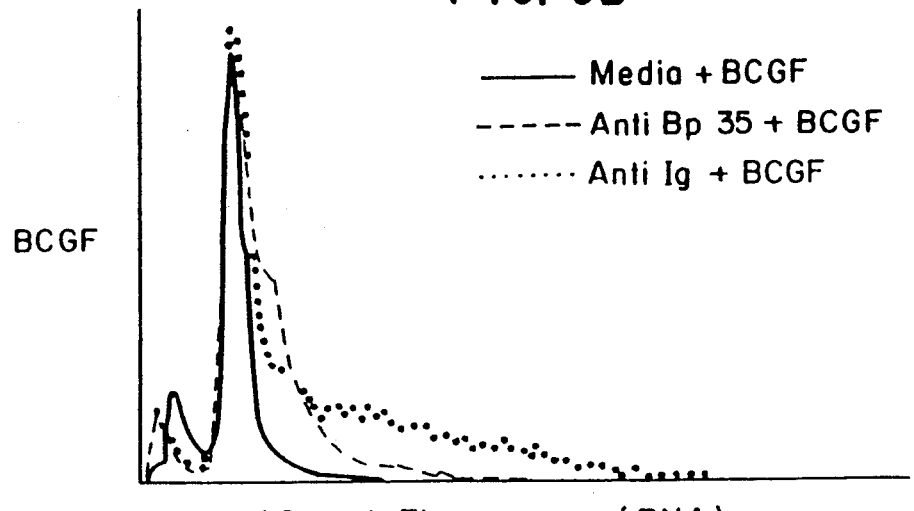

Anti-Bp35 alone, unlike anti-Bp50, can activate B-cells from $G_0$ to $G_1$ and thus can be referred to as an "activation" signal. Whether or not Bp35 functions only in early B-cell activation is not yet clear since anti-Bp35 antibodies can stimulate some B-cells to divide (Clark et al., 1985, Proc. Nat. Acad. Sci. USA 82:1766–1770). Similarly, Bp50 may not strictly function only as a "growth" signal: anti-Bp50 antibodies together with activation signals (anti-Bp35 or anti-u) not only augment proliferation but also augment the total number of B-cells entering $G_1$ (Table 2). In other words, anti-Bp50 as costimulant acts to promote the progression of both the activation ($G_0$ to $G_1$) and growth (G to S) phases of the cell cycle. The BCGF used in these studies also had similar activity (FIG. 6C). Thus, anti-Bp35 and anti-Bp50 (or BCGF) appear to be most analogous to the "competence" and "progression" factors described in studies of fibroblast growth regulation. How B-cells respond to anti-Bp35 or anti-Bp50 clearly may depend on their state of differentiation or activation.

Here we have shown that two mAb, anti-Bp35 (a "competence" signal) and anti-Bp50 (a "progression" signal), together can induce substantial proliferation of highly purified B-cells in the absence of antigen or other known factors. The natural ligands for these structures are not yet known. However, since mAb to appropriate epitopes can mimic both soluble factors and signals mediated by cell-cell interactions, it may be possible to use appropriate combinations of mAb to direct and regulate human B-cell proliferation or differentiation. This, in turn, will help in devising strategies in vivo for the control of human diseases such as B-cell malignancies, immunodeficiencies and certain autoimmune diseases.

The new monoclonal antibody, G28-5, that reacts with a single-chain polypeptide of approximately 50 Kd expressed on the surface of human B-cells is but a particular embodiment of the ligands of the present invention which can augment the proliferation of activated B-cells. Since human B-cell proliferation can be augmented similarly by T-cell-derived BCGFs including low- and high-molecular-weight BCGF we compared the activity of anti-Bp50 G28-5 with that of a BCGF preparation containing predominantly low-molecular-weight BCGF. Anti-Bp50 G28-5 and BCGF (low) were very similar in that they were costimulatory with the same activation agents (anti-Ig, anti-Bp35 and TPA) but were not costimulatory with each other or with IL-1 or IL-2. Furthermore, the activity of anti-Bp50 G28-5 was not dependent on its Fc domain since F(ab')$_2$ fragments of G28-5 were functionally active. This suggests that soluble anti-Bp50, like soluble BCGF, does not require Fc-receptor-bearing accessory cells to exert an effect. Furthermore, both anti-Bp50 and BCGF are effective only in the presence of an activation stimulus. In other words, anti-Bp50 and BCGF are not "competence" factors, but rather promote the "progression" of B-cells through the cell cycle.

While it is possible that Bp50 may function as receptor for a ligand such as a B-cell growth factor, several results suggest that Bp50 is not the receptor at least for the BCGF (low) used in this study: it is expressed on blood B-cells while BCGF (low) receptors apparently are not. Candidate structures for the BCGF (low) receptor, unlike Bp50, are also expressed only on activated B-cells. Furthermore, both normal and malignant B-cell populations differ in their responsiveness to anti-Bp50 versus BCGF (low) (Table 5 and FIG. 10). For instance, some B lymphomas proliferate in response to BCGF (low), but not in response to anti-Bp50. Finally, in a number of experiments, optimal concentrations of anti-Bp50 and BCGF together induced more proliferation than either one alone. Anti-Bp50 mimics the activity of other BCGF, such as BCGF (high) that are costimulatory with anti-IgM (Ambrus, et al., 1985, J. Exp. Med. 162:1319; Ambrus, et al., 1985, J. Clin. Invest. 75:732). This suggests that Bp50 could function as the receptor for BCGF (high).

Although Bp50 may be a receptor for a soluble ligand, alternatively, Bp50 may function as a receptor for a cell-cell mediated signal that regulates BCGF receptor levels and/or autocrine production. Precedence for differentiation antigens serving as amplifiers of an autocrine-receptor pathway comes from studies with T cells. MAb to the Lp220 common leukocyte antigen augments proliferation by elevating IL-2 receptor expression on activated T cells (Ledbetter, et al., 1985, J. Immunol. 135:1819). An analogous mechanism may be operating with anti-Bp50 and expression of certain BCGF receptors. Bp50 and BCGF (low) apparently are under some coordinate control since, like IL-1 and IL-2 receptors, BCGF augments expression of Bp50 on certain leukemic cells. The Bp50 molecule also shares similarities with the Tp44 molecule that functions to influence IL-2 production. We and others have shown that the 9.3 anti-Tp44 antibody augments proliferation of T cells activated by anti-CD3 or TPA (Ledbetter, et al., 1985, J. Immunol. 135:2331; Hara, et al., 1985, J. Exp. Med. 161:1513). Similarly, anti-Bp50 augments the proliferation of B-cells activated by anti-Bp35 or TPA. The Tp44 signal functions by stimulating IL-2 production rather than by stimulating T cell growth. The Bp50 signal presumably could function in an analogous manner by stimulating B-cell autocrine production (Gordon, et al., 1984, Nature, Lond. 310:145).

5.4.2. MODIFIED LIGANDS USED FOR IMMUNOSUPPRESSION OR TREATMENT OF MALIGNANACIES

According to this embodiment, the ligand of the present invention can be modified by the attachment of an antiproliferative agent so that the resulting molecule can be used to kill cells which express the Bp50 antigen. Such modified ligands may be used in the treatment of autoimmune disease in order to suppress the proliferation of B-cells and thereby suppress the autoimmune response. These modified ligands can also be used to immunosuppress a transplant patient to prevent rejection of a graft. Accordingly, cytotoxic agents which are used for the suppression of immune responses can be attached to the ligands of the invention. When using ligands which augment the proliferation of B-cells, an increased effect should result because the drug will be directed to proliferating B-cells.

In another embodiment, the ligands of the present invention which are modified by the attachment of an antiproliferative agent can be used to treat malignancies in which tumors or cells express the Bp50 antigen. Attachment of these chemotherapeutic agents to the ligands of the invention should result in a greater specificity of the drug for the malignant cells. Moreover, a particular advantage should be obtained when treating a B-cell malignancy with a ligand coupled to a cytotoxin which is more effective in killing proliferating cells than non-proliferating cells; treatment with such a ligand should result in a potentiation of the action of the cytotoxin.

Accordingly, the chemotherapeutic agents or antiproliferative agents which can be coupled to the ligands of the present invention include but are not limited to the agents listed in Table 6 below which is derived from Goodman and Gilman, The Pharmacological Basis of Therapeutics, Sixth Edition, MacMillan Publishing Co., Inc, New York, pp. 1249-1313, 1980 which is incorporated by reference herein.

TABLE 6

Chemotherapeutic Agents Which Can be Coupled to Anti-Bp50 Ligands

| Class | Type | Agent |
|---|---|---|
| Alkylating Agent | Nitrogen Mustard | Mechlorethamine |
| | | Cyclophosphamide |
| | | Melphalan |
| | | Uracil Mustard |
| | | Chlorambucil |
| | Ethylenimine Derivatives | Thiotepa |
| | Alkyl Sulfonates | Busulfan |
| | Nitrosoureas | Carmustine |
| | | Lomustine |
| | | Semustine |
| | | Streptozocin |
| | Triazenres | Dacarbazine |
| Antimetabolites | Folic Acid Analogs | Methotrexate |
| | Pyrimidine Analogs | Fluorouracil |
| | | Cytarabine |
| | | Azaribine |
| | Purine Anlogs | Mercaptopurine |
| | | Thioguanine |
| Natural Products | Vinca Alkaloids | Vinblastine |
| | | Vincristine |
| | Antibiotics | Dactinomycin |
| | | Daunorubicin |
| | | Doxorubicin |
| | | Bleomycin |
| | | Mithramycin |
| | | Mitomycin |
| | Enzymes | L-Asparaginase |
| Miscellaneous Agents | Platinum Coordinated Complexes | Cisplatin |
| | Substituted Urea | Hydroxyurea |
| | Methyl Hydrazine Derivative | Procarbazine |
| | Adrenocortical Suppressant | Mitotane |
| Hormones and Antagonists | Adrenocorticosteroids | Prednisone |
| | Progestins | Hydroxyprogesterone caproate |
| | | Medroprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| Radioactive Isotopes | Phosphorous | Sodium phosphate $^{32}P$ |

TABLE 6-continued

Chemotherapeutic Agents Which Can be Coupled to Anti-Bp50 Ligands

| Class | Type | Agent |
|---|---|---|
| | Iodine | Sodium Iodide $^{131}I$ |

Any method known in the art can be used to couple the ligand to the chemotherapeutic or antiproliferative agent. Examples of such methods have been enumerated previously (see Section 5, supra).

5 4.3. OTHER USES OF LIGANDS AND Bp50

In addition to the therapeutic applications the ligands and Bp5-0 itself have other applications in both in vitro and in vivo diagnostic assays, separation schemes, etc.

The Bp50 receptor can be used to manufacture and/or design the ligands of the invention. Bp50 can also be used with the ligands of the invention in assays in vitro which require a standard to quantify the amount of Bp50 detected in a sample. Ultimately, Bp50, itself may be useful as a soluble factor which mediates immunity, e.g. a lymphokine.

In addition to therapeutic treatment and diagnostic assays, the ligands of the present invention could be used for identifying or separating cells which express the Bp50 antigen. In addition, if an appropriate radiolabel or radio-opaque compound is linked to the ligand, the ligand could be used for in vivo imaging of tumors which express the Bp50 antigen. Other uses should become apparent to those skilled in the art from the foregoing description.

6. DEPOSIT OF CELL LINES

The following hybridoma has been deposited with the American Type Culture Collection, Rockville, Md., and has been assigned the listed accession number:

| Hybridoma | ATCC Accession Number |
|---|---|
| G28-5 | HB9110 |

The present invention is not to be limited in scope by the hybridoma deposited since the deposited embodiment is intended as a single illustration of one aspect of the invention and any cell lines which are functionally equivalent are within the scope of this invention. Indeed various modifications of the invention in addition to those shown and described herein will become apparent to those skilled in the art from the foregoing description and accompanying drawings. Such modifications are intended to fall within the scope of the appended claims.

What is claimed is:

1. A substantially pure 50 kilodalton B-cell surface antigen which is defined by monoclonal antibody G28-5.

* * * * *